(12) United States Patent
Brownell et al.

(10) Patent No.: US 10,603,270 B2
(45) Date of Patent: Mar. 31, 2020

(54) SKIN CARE COMPOSITIONS AND METHODS OF USE THEREOF

(71) Applicants: Unigen, Inc., Seattle, WA (US); Unigen, Inc., Cheonan-si, Chungcheongnam-do (KR)

(72) Inventors: Lidia Alfaro Brownell, Tacoma, WA (US); Min Chu, Newcastle, WA (US); Brandon Corneliusen, Tenino, WA (US); Mei-Feng Hong, Seattle, WA (US); Ji-Hye Hwang, Jecheon-si (KR); Eu-Jin Hyun, Cheongan-si (KR); Qi Jia, Olympia, WA (US); Ping Jiao, Newcastle, WA (US); Mi-Ran Kim, Daejeon (KR); Bo-Su Lee, Pohang-si (KR); Young-Chul Lee, Daejeon (KR); Jeong-Bum Nam, Cheongju-si (KR); Mi-Sun Oh, Chungcheongnam-do (KR); Mesfin Yimam, Tacoma, WA (US)

(73) Assignee: Unigen, Inc., Tacoma, WA (US)

( * ) Notice: Subject to any disclaimer, the term of this patent is extended or adjusted under 35 U.S.C. 154(b) by 766 days.

(21) Appl. No.: 15/031,709

(22) PCT Filed: Oct. 30, 2014

(86) PCT No.: PCT/US2014/063203
§ 371 (c)(1),
(2) Date: Apr. 22, 2016

(87) PCT Pub. No.: WO2015/066352
PCT Pub. Date: May 7, 2015

(65) Prior Publication Data
US 2016/0263013 A1   Sep. 15, 2016

Related U.S. Application Data

(60) Provisional application No. 61/897,690, filed on Oct. 30, 2013.

(51) Int. Cl.
| | | |
|---|---|---|
| A61K 8/97 | (2017.01) | |
| A61Q 19/00 | (2006.01) | |
| A61K 8/49 | (2006.01) | |
| A61Q 19/08 | (2006.01) | |
| A61K 8/02 | (2006.01) | |
| A61Q 19/06 | (2006.01) | |
| A61K 8/36 | (2006.01) | |

(52) U.S. Cl.
CPC .............. *A61K 8/97* (2013.01); *A61K 8/0204* (2013.01); *A61K 8/36* (2013.01); *A61K 8/4926* (2013.01); *A61K 8/4973* (2013.01); *A61Q 19/00* (2013.01); *A61Q 19/06* (2013.01); *A61Q 19/08* (2013.01); *A61K 2800/42* (2013.01); *A61K 2800/522* (2013.01); *A61K 2800/5922* (2013.01)

(58) Field of Classification Search
CPC ........ A61K 36/57; A61Q 19/00; A61Q 19/08; A61Q 17/04
See application file for complete search history.

(56) References Cited

U.S. PATENT DOCUMENTS

| | | | | |
|---|---|---|---|---|
| 2004/0101584 A1* | 5/2004 | McLaughlin | ........ | A61K 31/341 424/769 |
| 2012/0148636 A1 | 6/2012 | Berrido et al. | | |

FOREIGN PATENT DOCUMENTS

| | | | |
|---|---|---|---|
| BR | 200401062 A | * | 9/2005 |
| CA | 2778340 | | 4/2011 |
| JP | 2009269842 | | 11/2009 |

OTHER PUBLICATIONS

Nirban A A "A Study on Indigenous Technical Knowledge About Rice Cultivation and Bovine Health Management Practices in Konkan Region of Maharashtra" Thesis, Dharwad University of Agricultural Sciences, Jan. 2006, 305pp. (Year: 2006).*
Gaidos S "Pawpaw research results in new product for head lice" Purdue News, Sep. 20, 2001, 2 pages. (Year: 2001).*
International Preliminary Report on Patentability, PCT/US2014/063203, dated May 3, 2016, 8 pages.
Official Action, Canada Patent Office, CA 2927499, dated May 25, 2016, 5 pages.
PCT Search Report, PCT/US2014/063203, dated Feb. 11, 2015, 3 pages.
PCT Written Opinion, PCT/US2014/063203, dated Feb. 11, 2015, 7 pages.

* cited by examiner

*Primary Examiner* — Aaron J Kosar
(74) *Attorney, Agent, or Firm* — D. Sandra Thompson; Finlayson Toffer Roosevelt & Lilly

(57) ABSTRACT

The present disclosure provides a mixture of sugar apple and rosemary extracts, optionally in combination with prickly ash extract, for use as skin care compositions.

10 Claims, No Drawings

SKIN CARE COMPOSITIONS AND METHODS OF USE THEREOF

This application is a National Stage application claiming priority to Patent Cooperation Treaty Serial Number PCT/US2014/063203 entitled "Skin Care Compositions and Methods of Use Thereof" filed on Oct. 30, 2014, which claims priority to U.S. Provisional Patent Application Ser. No. 61/897,690 filed on Oct. 30, 2013, all of which are incorporated herein by reference in their entirety.

BACKGROUND

Adipose tissue is a specialized connective tissue that functions as the major storage site for fat in the form of triglycerides. Lipogenesis is the synthesis, and eventual deposition of fat, which is a process that occurs in adipose tissue and in the liver. Carbohydrate and protein consumed in the diet can be converted into fat. Carbohydrates can be stored as glycogen in the liver and muscle, and can also be converted into triglycerides in the liver and transferred to adipose tissue for storage. Amino acids from proteins are used for new protein synthesis or they can be converted into carbohydrate and fat. Fatty acids, in the form of triglycerides, are derived from the diet or synthesized by the liver. Very little synthesis of free fatty acids occurs in the cells of adipose tissue (adipocytes). Triglycerides are the most abundant source of fatty acids since this is the form in which dietary lipids are assembled by the digestive system and liver, and then stored in adipose tissue. Triglycerides are made up of long chain of fatty acids, which are hydrolyzed into glycerol and free fatty acids by an enzyme called lipoprotein lipase (LPL). The free fatty acids are taken up by adipocytes and stored again as triglycerides through a complex process.

Sometimes, adipocytes will store excess fat and lead to the formation of cellulite. Cellulite is dimpled, lumpy or puckered skin caused by pockets of herniated subcutaneous fat that bulges into the dermis between collagen fibers that connect skin to muscle. Cellulite is a common problem that affects 80-90% of post-adolescent females, which generally occurs on the thighs, hips, and abdomen since the fat distribution in these areas is closer to the skin. In the medical field, cellulite may be referred to as adiposis edematosa, dermopanniculosis deformans, status protrusus cutis, and gynoid lipodystrophy. Cellulite is informally referred to as orange peel syndrome, cottage cheese skin, hail damage, and the mattress phenomenon. Although the causes of cellulite are not well understood, several factors are believed to be associated with this disorder, including hormonal factors, genetics, and life-style factors (e.g., lack of exercise, unhealthy diet). Clinically, cellulite is not considered a pathological condition, but it is a complex problem involving the microcirculatory system and lymphatics, the extracellular matrix, alterations to connective tissue, and subtle inflammatory alterations.

Currently, there are no effective skin care products to address cellulite and associated skin problems, although significant efforts have been made to develop anti-cellulite agents over the past few decades. For example, there are several physical and mechanical therapies that have been suggested to remove cellulite for body slimming, such as pneumatic massages, massages that stimulate lymphatic flow, heat therapy, ultrasound therapy, radio frequency therapy, magnetic therapy, radial wave therapy, electrical stimulation, and laser treatment. But, none of these approaches are highly effective and none provide a long term or permanent solution. More importantly, all these methods include high costs (on average, several thousand dollars for the treatments).

BRIEF SUMMARY

In brief, the present disclosure is directed to compounds and compositions useful for skin care, body slimming and reducing cellulite, including stereoisomers, pharmaceutically or dermatologically acceptable salts, tautomers, and prodrugs of the disclosed compounds, and to related methods for tightening and improving firmness of sagging skin, improving skin tone, improving skin elasticity, reducing water retention for smoother and tighter skin, and reducing fat deposits in cutaneous tissues.

In certain embodiments, this disclosure provides a composition comprising an *Annona* (also known as *Anona*) extract, wherein the *Annona* extract is optionally enriched for one or more acetogenins (such as squamocin, motrilin), kaurenoic acid, or both. In further embodiments, this disclosure provides a composition comprising a mixture of an *Annona* extract and a *Zanthoxylum* extract, wherein the *Annona* extract is optionally enriched for one or more acetogenins (such as squamocin, motrilin), kaurenoic acid, or both, and the *Zanthoxylum* extract is optionally enriched for one or more isoquinoline alkaloids (such as magnoflorine, lauriflorine). In still further embodiments, this disclosure provides a composition comprising a mixture of an *Annona* extract and a *Rosmarinus* or *Slavia* extract, wherein the *Annona* extract is optionally enriched for one ore more acetogenins (such as squamocin, motrilin), kaurenoic acid, or both, and the *Rosmarinus* or *Slavia* extract is optionally enriched for one or more terpenoids (such as carnosic acid, carnosol). In other embodiments, this disclosure provides a composition comprising a mixture of an *Annona* extract, a *Zanthoxylum* extract, and a *Rosmarinus* or *Slavia* extract, each optionally enriched for the compounds noted above. In still other embodiments, the compositions further contain one or more adjuvant, such as a contouring agent, a skin toner, a lipolysis promoting agent, a circulation improving agent, or any combination thereof. In certain embodiments, a biomarker for an *Annona* extract enriched for one or more acetogenins is a terpenoid, such as kaurenoic acid (e.g., when at least 1% kaurenoic acid is present in the extract).

In another aspect, the present disclosure provides methods for improving skin appearance and body slimming. In certain embodiments, compositions of this disclosure can be used in methods for tightening and firming sagging or loose skin, managing or controlling or reducing or preventing the effect of skin aging (anti-aging), managing or controlling or reducing or preventing age spots, improving skin tone, improving skin elasticity, smoothing or toning skin, promoting skin rejuvenation, reducing water retention for smoother and tighter skin, moisturizing skin, controlling or reducing bruises or bruising, protecting against free radical damage, reducing fat deposits in cutaneous tissue, managing or controlling or reducing or preventing cellulite, inhibiting cellulite formation, managing or controlling or reducing or preventing stretch marks, reducing fat synthesis, reducing fat content in cells (e.g., adipocytes), reducing fat cell size, reducing or inhibiting cell differentiation into fat cells, promoting fat cell apoptosis, promoting lipolysis, improving fat removal, maintaining or promoting or supporting a healthy lipid profile, maintaining or promoting or supporting a healthy cholesterol level, promoting weight loss, reducing body mass index (BMI), managing or reducing thigh or arm circumference, reducing or managing or controlling double chin, reducing or managing or controlling periorbital puffiness or suborbicularis oculi fat or eye bags, promoting weight control, supporting weight management, promoting collagen synthesis, promoting hyaluronic acid synthesis, improving or activating microcirculation (e.g., cutaneous), maintaining or supporting cardiovascular function, supporting immune function, maintaining or promoting or supporting healthy blood sugar level, or any combination thereof. In each of these embodiments, the compositions of this disclosure are administered topically.

These and other aspects of the invention will be apparent upon reference to the following detailed description.

DETAILED DESCRIPTION

The present disclosure provides compositions and methods for the use of one or more acetogenins, optionally combined with one or more isoquinoline alkaloids (such as aporphine alkaloids), one or more terpenoids (such as phenolic diterpinoids), or any combination thereof for body slimming, treating cellulite, skin care, or skin toning. For example, acetogenins (such as squamocin, motrilin) may be contained in or isolated from an *Annona* extract, isoquinoline alkaloids (such as magnoflorine, lauriflorine) may be contained in or isolated from a *Zanthoxylum* extract, and terpenoids (such as carnosic acid) may be contained in or isolated from a *Rosmarinus* or *Salvia* extract. An unexpected result of compositions combining one or more acetogenin with one or more isoquinoline alkaloid, terpenoid, or both is that they function synergistically to, for example, increase inhibition of lipid accumulation and intracellular triglyceride accumulation, improve cardiovascular function (vasorelaxation effect and inhibition of platelet aggregation), and exhibit an anti-oxidation function. In a related aspect, this disclosure provides methods for conditioning, firming, tightening, or toning skin in an individual having a condition or disorder associated with skin appearance, such as cellulite, excess weight, age, or the like.

In certain embodiments, the present disclosure provides anti-cellulite compositions and methods for using the same. In further embodiments, a composition of the present disclosure can be formulated with one or more known body slimming, anti-cellulite, or skin conditioning agents.

In the following description, certain specific details are set forth in order to provide a thorough understanding of various embodiments of this disclosure. However, one skilled in the art will understand that the invention may be practiced without these details.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double or triple bonds), having from one to twelve carbon atoms ($C_1$-$C_{12}$ alkyl), or one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, or the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, or having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of this disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl), wherein at least one hydrogen atom is replaced by a bond to a non-hydrogen atoms such as a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl group. In addition, each of the foregoing substituents may also be optionally substituted with one or more of the above substituents.

"Glycoside" refers to a molecule in which a sugar group is bonded through its anomeric carbon to another group via a glycosidic bond. Exemplary sugars include glucose, rhamnose, manose, galactose, arabinose, glucuronide and others. Glycosides can be linked by an O- (an O-glycoside), N- (a glycosylamine), S-(a thioglycoside), or C- (a C-glycoside) glycosidic bond. Compounds of this disclosure can form glycosides at any suitable attachment point.

"Prodrug" is meant to indicate a compound that may be converted under physiological conditions or by solvolysis to a biologically active compound of this disclosure. Thus, the term "prodrug" refers to a metabolic precursor of a compound of this disclosure that is pharmaceutically or dermatologically or cosmetically acceptable.

A prodrug may be inactive when administered to a subject in need thereof, but is converted in vivo to an active compound of this disclosure. Prodrugs are typically rapidly transformed in vivo to yield the parent compound of this disclosure, for example, by hydrolysis in blood. The prodrug compound often offers advantages of solubility, tissue compatibility or delayed release in a mammalian organism (see Bundgard, H., Design of Prodrugs (1985), pp. 7-9, 21-24 (Elsevier, Amsterdam)). A discussion of prodrugs is provided in Higuchi et al., A.C.S. Symposium Series, Vol. 14, and in Bioreversible Carriers in Drug Design, Ed. Edward B. Roche, American Pharmaceutical and Nutraceutical Association and Pergamon Press, 1987.

The term "prodrug" is also meant to include any covalently bonded carriers, which release the active compound of this disclosure in vivo when such prodrug is administered to a mammalian subject. Prodrugs of a compound of this disclosure may be prepared by modifying functional groups present in the compound of this disclosure in such a way that the modifications are cleaved, either in routine manipulation or in vivo, to the parent compound of this disclosure. Prodrugs include compounds of this disclosure wherein a hydroxy, amino or mercapto group is bonded to any group that, when the prodrug of the compound of this disclosure is administered to a mammalian subject, cleaves to form a free hydroxy, free amino or free mercapto group, respectively. Examples of prodrugs include acetate, formate and benzoate derivatives of alcohol or amide derivatives of amine functional groups in the compounds of this disclosure and the like.

The instant disclosure is also meant to encompass all pharmaceutically or dermatologically acceptable compounds of this disclosure being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of this disclosure, for example, those incorporating a radioactive isotope, are useful in drug or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of this disclosure can generally be prepared by conventional techniques known to those skilled in the art or by processes analogous to those described in the Preparations and Examples as set out below using an appropriate isotopically-labeled reagent in place of the non-labeled reagent previously employed.

The instant disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, this disclosure includes compounds produced by a process comprising administering a compound of this invention to a mammal for a period of time sufficient to yield a metabolic product thereof. Such products are typically identified by administering a radiolabelled compound of this disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals, such as laboratory animals or household pets (e.g., cats, dogs, swine, cattle, sheep, goats, horses, rabbits), and non-domestic animals, such as wildlife or the like.

"Optional" or "optionally" means that the subsequently described element, component, event or circumstance may or may not occur, and that the description includes instances where the element, component, event or circumstance occur and instances in which they do not. For example, "optionally substituted aryl" means that the aryl radical may or may not be substituted and that the description includes both substituted aryl radicals and aryl radicals having no substitution.

"Pharmaceutically or dermatologically or cosmetically acceptable carrier, diluent or excipient" includes any adjuvant, carrier (e.g., cetearyl alcohol), excipient, astringent, glidant, essential oil (e.g., Rosemary Moroccan oil, Geranimum Rose Egyptian, Lavender Bulgarian), diluent, preservative (e.g., a blend of phenoxyethanol, caprylyl alcohol, ethylhexyl glycerin and hexylene glycol), dye/colorant, defoamer (e.g., polydimethylsiloxane), surfactant, emollient (e.g., $C_{12-15}$ alkyl benzoate), moisturizer (e.g., ethylhexyl stearate), wetting agent, dispersing agent, suspending agent, stabilizer, isotonic agent, solvent, or emulsifier that has been approved by the United States Food and Drug Administration as being acceptable for use in humans or domestic animals.

"Pharmaceutically or dermatologically or cosmetically acceptable salt" includes both acid and base addition salts.

"Pharmaceutically or dermatologically or cosmetically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

"Pharmaceutically or dermatologically or cosmetically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of the compound of this disclosure. As used herein, the term "solvate" refers to an aggregate that comprises one or more molecules of a compound of this disclosure with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. Compounds of this disclosure may be true solvates, while in other cases, compounds of this disclosure may merely retain adventitious water or be a mixture of water plus some adventitious solvent.

In the process of making compounds of this disclosure, it will also be appreciated by those skilled in the art that functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

A "pharmaceutical composition" or "dermatological composition" or "cosmetic composition" refers to a formulation of a compound of this disclosure and a medium generally accepted in the art for the delivery of the biologically active compound to mammals, e.g., humans. For example, a pharmaceutical composition of the present disclosure may be formulated or used as a stand alone composition, or as a component in or for use in conjunction with a prescription drug, an over the counter (OTC) medicine, a botanical drug, an herbal medicine, a homeopathic agent, or any other form of health care product reviewed and approved by a government agency. Exemplary dermatological compositions of the present disclosure may be formulated or used as a stand alone composition, or as a cosmetic or bioactive component in creams, gels, lotions, or herbal products. A medium generally accepted in the art includes all pharmaceutically, dermatologically or cosmetically acceptable carriers, diluents or excipients therefor.

As used herein, "enriched for" refers to a plant extract or other preparation having at least a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than 50%, 25%, 20%, 15%, 10%, 5%, 1%, 0.5%, or 0.1% of the components contained in an extract) but still provide most of the desired biological activity. Any composition of this disclosure containing a major active ingredient may also contain minor active ingredients that may or may not contribute to the pharmaceutical or dermatological or cosmetic activity of the enriched composition, but not to the level of major active components, and minor active components alone may not be effective in the absence of a major active ingredient.

"Effective amount" or "therapeutically effective amount" refers to that amount of a compound or composition of this disclosure which, when administered to a mammal, such as a human, is sufficient to effect treatment, including any one or more of: (1) treating, managing, controlling or preventing cellulite; (2) promoting lipolysis; (3) suppressing cell differentiation into fat cells; (4) reducing fat synthesis or accumulation; (5) treating, reducing or preventing sagging or loose skin, effect of aging on skin, age spots, stretch marks; (6) improving, supporting or promoting skin elasticity, skin tone, skin smoothness, skin firmness, skin rejuvenation; and (7) increasing, improving or activating microcirculation. The amount of a compound or composition of this disclosure that constitutes a "therapeutically effective amount" will vary depending on the compound, the condition being treated and its severity, the manner of administration, the duration of treatment, or the age of the subject to be treated, but can be determined routinely by one of ordinary skill in the art having regard to his own knowledge and to this disclosure.

"Supplements" as used herein refer to a product that improves, promotes, increases, rejuvenates, manages, controls, maintains, optimizes, modifies, reduces, inhibits, or prevents a particular condition associated with a natural state or biological process (i.e., are not used to diagnose, treat, mitigate, cure, or prevent disease). In certain embodiments, a supplement is a dietary supplement. In certain other embodiments, dietary supplements are a special category of food and are not a drug. In futher embodiments, supplements are useful for topical application and not for oral administration or ingestion. For example, with regard to skin care, body slimming or anti-cellulite compositions, a topical supplement may be used to provide a fresh scent (essential oil), a moisturizer, a contouring agent, a skin toner, a lipolysis promoting agent, a circulation improving agent, or the like.

"Treating" or "treatment" or "ameliorating" refers to either a therapeutic treatment or prophylactic/preventative treatment of a disease or condition of interest in a mammal, such as a human, having or suspected of having a disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., fat accumulation, cellulite, skin aging) without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, "statistical significance" refers to a p value of 0.050 or less as calculated using the Students t-test and indicates that it is unlikely that a particular event or result being measured has arisen by chance.

The chemical naming protocol and structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

It should be understood that in the present description, combinations of substituents or variables of the depicted formulae are permissible only if such contributions result in stable compounds.

As noted herein, in certain embodiments, the present disclosure provides a skin care composition comprising acetogenins. Structurally, acetogenins are a class of $C_{35}/C_{37}$ natural products derived from $C_{32}/C_{34}$ fatty acids that have been combined with a 2-propanol unit. They are usually characterized by a long alphatic chain bearing a terminal methyl-substituted α,β-unsaturated γ-lactone ring (sometimes rearranged to a kelolactone), with one, two or three tetrahydrofuran (THF) rings or epoxides and/or one, two or more double bonds located along the hydrocarbon chain and a number of oxygenated moieties of hydroxyls, acetoxyls, ketones, and epoxides (Alali et al., *J. Nat. Prod.* 62:504, 1999). Acetogenins, a class of bioactive secondary plant metabolites, can be found in most genera of the family Annonaceae, such as *Accopetalum, Annona* (also known as *Anona*), *Aplysia, Asimina, Asparagopsis, Aspergillus, Chondria, Dasymaschalon, Dasyphila, Goniothalamus, Hali-* clona spp., *Laurencia, Miliusa, Mycale, Ophrypetalum, Phacelocarpus, Polyalthia, Porcelia, Ptilonia, Rollinia, Saccopetalum, Spongia, Uvaria*, and *Xylopia*.

In certain embodiments, acetogenins are extracted, enriched, isolated, or purified from an *Annona* (also referred to as *Anona*) plant, which may also include terpenoid biomarkers (e.g., kaurenoic acid). *Annona* plants are tropical evergreen trees that produce a large, heart-shaped, edible fruit that is popular in South America and is in the pawpaw/sugar apple family, Annonaceae. The ripe sugar apple (*Annona squamosa*) is usually broken open and the fleshy segments eaten. In Malaysia, the flesh is pressed through a sieve to eliminate the seeds and is then added to ice cream or blended with cold milk to make a cool beverage and never cooked (see Alali et al., *J. Nat. Prod.* 62:504, 1999; Morton, J. 1987. Sugar Apple. p. 69-72. In: Fruits of warm climates. Julia F. Morton, Miami, Fla.). Exemplary *Annona* species include *A. atemoya, A. cherimola, A. cherimolia, A. coriacea, A. crassiflora, A. glabra, A. glauca, A. jahnii, A. longifolia, A. montana, A. muricata, A. nutans, A. pupurea, A. reticulata, A. sengalensis, A. spinescens, A. spraguei, A. squamosa, A, recticulata*, and *A. triloba*.

In certain embodiments, an acetogenin compound of the present disclosure has a structure according to formula (A) as follows:

$$R^1\text{-L-}R^2\text{—}R^3 \quad (A)$$

wherein $R^1$ is a linear $C_{5\text{-}20}$ optionally substituted with 0 to 10 —OH, —C(=O)$R_g$, —C(=O)O$R_g$, and containing from 0 to 2 double bonds;

wherein $R_g$ is the same or different and independently hydrogen or $C_{1\text{-}5}$ alkyl;

wherein L is a group selected from a tetrahydrofuran group of structure (B), an epoxy group of structure (C), a heterocycle group of structure (D), $C_{1\text{-}5}$ alkyl, a

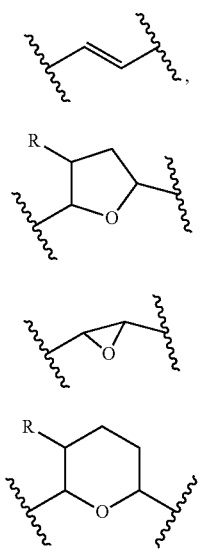

B

C

D or a group of formula $L^1\text{-}(X\text{-}L^2)_p$, wherein $L^1$ and $L^2$ are independently selected from a tetrahydrofuran group of structure (B), an epoxy group of structure (C), a heterocycle group of structure (D), $C_{1\text{-}5}$ alkyl, and a

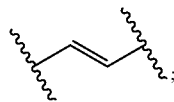

wherein R is H or —OH, and X is a $C_{0\text{-}5}$ alkyl optionally substituted with —OH;

wherein $R^2$ is a linear $C_{5\text{-}20}$ optionally hyrdroxylated or carboxylated and containing from 0 to 2 double bonds;

wherein $R^3$ is a lactone moiety selected from

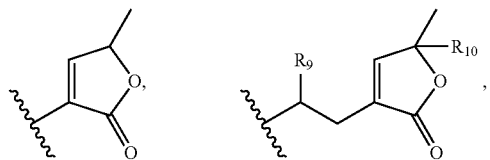

cis or trans

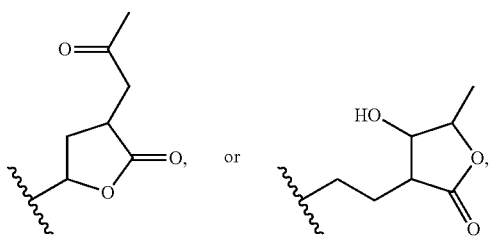 [SMILES: *C1CC(CC(C)=O)C(=O)O1 ; "or" ; *CCC1C(=O)OC(C)C1O]

wherein in $R_9$ and $R_{10}$ are independently H or —OH.

In certain other embodiments, an acetogenin compound of the present disclosure has structure according to formula (I), (II), or (III), as follows:

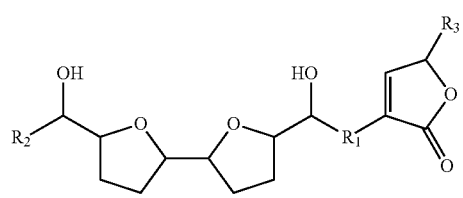

I

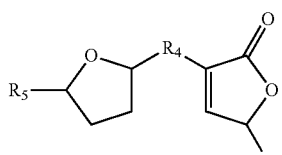

II

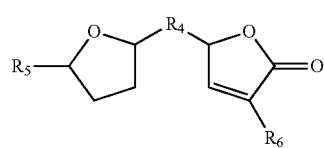

III wherein $R_1$-$R_6$ are each independently substituted or unsubstituted $C_{0\text{-}50}$ alkyl or rings having from $C_{0\text{-}50}$ and/or 0-5 tetrahydrofuran rings and/or double and/or triple bonds and/or having moieties of hydroxyls, acetoxyls, ketones and/or epoxides located along the hydrocarbon chains or rings.

Exemplary acetogenins include bulladecin, bullatacin, squamocin (annonin I), annonacin, annonisin, articulin, asiminacin, atemotetrolin, carolin A, carolin B, carolin C, motrilin (squamocin C), annoglaucin, bullacin, bullatacin, bullatetrocin, cohibin A, cohibin B, diepomuricanin B, diepoxyrollin, donnaienin D, epomusenin A, epomusenin B, espelicin, gigantecinone, glabracin A, glabracin B, glaucanetin, goniotriocin, goniotrionin, goniotetracin, guanaconne, 9-hydroxyasimicinone, jimenezin, membrarollin, microcarpacin, molvizarin, montecristin, mosinon A, muconin, mucoxin, muridienin-1, muridienin-2, parviflorin, pyranicin, pyragonicin, rollidecin C, rollidecin D, rollimembrin, rollitacin, rollinacin, spinencin, squamocin D, trilobacinone, trilobalicin, uvaricin, uvarigin, uvarigrandin A, uvariasolin I, uvariasolin II, xylomatenin, annonacin A, purpurediolin, and purpurenin.

In other embodiments, the present disclosure provides a skin care or body slimming composition comprising isoquinoline alkaloids. Alkaloids are basic nitrogenous organic compounds of plant origin. Isoquinoline alkaloids are a class of alkaloids derived from isoquinoline, which includes aporphine alkaloids and benzophenanthridine alkaloids. Isoquinoline has the following structure:

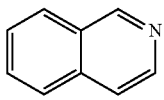

Aporphine alkaloids and benzophenanthridine alkaloids have been isolated from the genera of more than twenty plant families, including Araceae, Aristolochiaceae, Berberidaceae, Euphorbiaceae, Helleboraceae, Lauraceae, Magnoliaceae, Menispermaceae, Papaveraceae, Ranunculaceae, Rhamnaceae and Rutaceae. Within these plant families, these alkaloids have been isolated from species in numerous genera, including *Aconitum, Aristolochia, Berberis, Chelidonium, Clemnatis, Cocculus, Coplis, Dioscoreophyllum, Epimedium, Fumaria, Glaucium, Magnolia, Mahonia, Manodora, Nandina, Pachygone, Phellodendron, Ranunculus, Sinomenium, Thalictrum, Tinospora* and *Zanthoxylum*.

In certain embodiments, isoquinoline alkaloids are extracted, isolated, or purified from a *Zanthoxylum* plant. *Zanthoxylum* (also referred to in the literature as *Xanthoxylum*), a member of the Yellow Wood family (Rutaceae), is a widely distributed genus of plants that includes more than thirty species. Two species of *Zanthoxylum* are indigenous to the mainland of the United States—*Z. americanum* Mill. (Northern Prickly Ash) and *Z. clava-herculis* L. (Southern Prickly Ash)—these two species can be referred to as Prickly Ash. Northern Prickly Ash is native to southern Canada and northern, central and western parts of the United States, while Southern Prickly Ash is native to central and southern United States. Prickly Ash is a shrub or small tree that grows to 5-10 feet in height, and is commonly known as the toothache tree since it is used as a traditional native North American remedy for toothaches. Exemplary *Zanthoxylum* species include *Z. albuqurquei, Z. alatum, Z. americanum, Z. bungeanum, Z. belizense, Z. clava-herculis, Z. coco, Z. coriaceum, Z. dipetalum, Z. flavum, Z. gentlei, Z. kauaense, Z. nitidum, Z. piasezkii, Z. piperitum, Z. quinduense, Z. thomasianum*, and *Z. zanthoxyloides*.

In certain embodiments, an aporphine alkaloid compound of the present disclosure has a structure according to formula (IV), as follows:

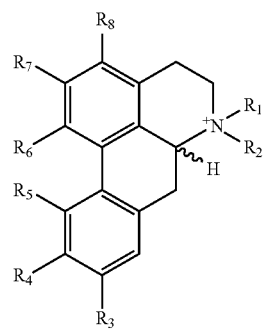

wherein $R_1$ and $R_2$ are independently selected from the group consisting of H, alkyl, substituted alkyl, cycloalkyl, substituted cycloalkyl, alkenyl or substituted alkenyl, methylene; $R_3$—$R_8$ are each independently H, hydroxy, thiol, methoxy, methyl sulfide, methylenedioxy, alkoxy, alkyl sulfide or pharmaceutically acceptable acid addition salts, selected from chloride, iodide, fluoride, sulfate, phosphate, acetate, or carbonate. In certain other embodiments, an aporphine alkaloid is Magnoflorine, wherein $R_1$ and $R_2$ are —$CH_3$; $R_3$ and $R_8$ are H; $R_4$ and $R_7$ are —$OCH_3$; and $R_5$ and $R_6$ are —OH. In still other embodiments, an aporphine alkaloid is laurifoline, wherein $R_1$ and $R_2$ are —$CH_3$; $R_3$ and $R_6$ are —OH; $R_4$ and $R_7$ are —$OCH_3$; and $R_5$ and $R_6$ are H.

In certain other embodiments, a benzophenanthridine alkaloid compound of the present disclosure has a structure according to formula (V), as follows:

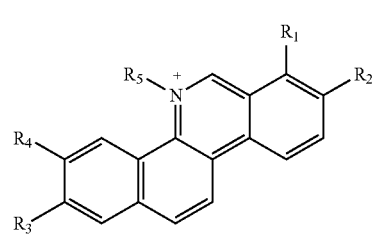

wherein $R_1$-$R_4$ are each independently H, hydroxy, alkoxy, methoxy, methylenedioxy, thiol, methyl sulfide or alkyl sulfide; and $R_5$ is H, alkyl, substituted alkyl, cycloalkyl, substituted cycloalkyl, alkenyl or substituted alkenyl.

In other embodiments, the present disclosure provides a skin care or body slimming composition comprising terpenoids. *Rosmarinus*, commonly known as Rosemary, is a woody, perennial herb with fragrant, evergreen, needle-like leaves and white, pink, purple, or blue flowers. Rosemary is a member of the mint family Lamiaceae, which includes many other herbs, and is native to the Mediterranean region. Rosemary extracts contain several bioactive ingredients, including terpenoids (e.g., mono-, di-, triterpenoids). A common class of compounds are the phenolic diterpenes, with the most abundant being carnosic acid. Phenolic diterpenes are not only found in *Rosmarinus* extracts, but also *Salvia* extracts. Exemplary *Rosmarinus* species include *R. officinalis, R. tomentosus, R. eriocalyx*, and *R. palaui*. Exemplary *Salvia* species include *S. apiana, S. canariensis, S. candelabrum, S. cardiophylla, S. columcariae, S. cryptantha, S. hypargeia, S. officinalis, S. lanigera, S. miltiorrhiza, S. munzil, S. phlomoides, S. pubescens, S. prionitis*, and *S. texana*.

Exemplary phenolic diterpenes found in these plants include carnosic acid (also known as salvin), 16-hydroxycarnosic acid, 11-acetoxycarnosic acid, methylcarnosoate, 7-oxocarnosic acid, 6-oxo-7-β-hydroxy carnosic acid, carnosol, isorosmanol, 12-hydroxyisocarnosol, 11,12-methyoxy-isorosmanol, rosmanol, epirosmanol, 7-monomethylepirosmanol, rosmaridiphenol, galdosol, carnosic acid 12-methylether-δ-lactone, arucatriol, deoxocarnosol 12-methylether, 6-α-hydroxydemethylcryptojaponol, salvicanol, 11,12-dimethoxy-6,8,11,13-tetraen-20-oic acid methylester, rosmanol-carnosoate, candesalvone A, 2-α-hydroxysugiol, 7-ethoxyrosmanol, 20-deoxocarnosol, 3-β-hydroxy-demethylcryptojapan, salvinolone, 6,7-dehydroxysalviol, or the like.

It is understood that any embodiment of the compounds of structures (I) to (V) of this disclosure, and any specific substituent set forth herein for the compounds of structures (I) to (V) of this disclosure, may be independently combined with other embodiments or substituents of any one of the compounds of structures (I) to (V) of this disclosure to form embodiments of this disclosure not specifically set forth herein. In addition, in the event that a list of substituents is listed for any particular R group in a particular embodiment or claim, it is understood that each individual substituent may be deleted from the particular embodiment or claim and that the remaining list of substituents will be considered to be within the scope of this disclosure.

Compounds of this disclosure can be extracted, isolated or purified from plant sources, for example, from plant genera or plant species or certain plant parts (e.g., bark, leaves, fruits) included in the Examples and elsewhere throughout the present application. Alternatively or in addition, compounds of this disclosure can be prepared synthetically or semi-synthetically. In certain embodiments, one or more compounds of this disclosure are enriched for or are the major active ingredients in a fresh pressing or an extract from an indicated plant genus or plant species, wherein the fresh pressing or enriched extract is obtained from a whole plant or certain plant parts, such as leaves, bark, trunk, trunk bark, stem, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. In some related embodiments, compounds are isolated from plant sources and synthetically modified to contain any of a variety of substituents (see, e.g., Vieira et al., *J. Braz. Chem. Soc.* 13:151, 2002). In this regard, synthetic modification of the compound isolated from plants can be accomplished using any number of techniques that are known in the art and well within the knowledge of one of ordinary skill in the art.

The bioactive acetogenins of this disclosure may be obtained by synthetic methods or extracted from one or more plants, such as *Annona*. In certain embodiments, an *Annona* extract is from *Annona squamosa*, or an *Annona* extract is a mixture of extracts from one, two, three, four or more *Annona* species.

In further embodiments, an *Annona squamosa* extract is enriched for one or more acetogenins, such as squamosin, motrilin, or both. In still further embodiments, an *Annona* extract enriched for squamosin, motrilin, or both is a combination of extracts from one, two, three, four or more *Annona* species. In yet further embodiments, there is provided isolated, partially purified, or substantially purified squamosin, motrilin, or both from an *Annona* extract. In certain embodiments, an *Annona* extract enriched for acetogenins contains at least about 0.005% at least about 0.01%, at least about 0.05% at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 12%, at least about 15%, at least about 16%, at least about 17%, at least about 18%, at least about 19%, at least about 20%, at least about 21%, at least about 22%, at least about 23%, at least about 24%, at least about 25%, or at least about 30% acetogenins. In other embodiments, an *Annona* extract enriched for acetogenins contains from about 0.5% to about 30%, or from about 1% to about 18%, or from about 3% to about 23%, or from about 2% to about 9% acetogenins. In certain other embodiments, a biomarker for an *Annona* extract enriched for one or more acetogenins is a terpenoid, such as kaurenoic acid. In still certain other embodiments, a biomarker for an *Annona* extract enriched for one or more acetogenins is kaurenoic acid, wherein the extract comprises at least 1% kaurenoic acid.

The bioactive isoquinoline alkaloids of this disclosure may be obtained by synthetic methods or extracted from one or more plants, such as *Zanthoxylum*. In certain embodiments, a *Zanthoxylum* extract is from *Zanthoxylum americanum, Zanthoxylum clava-herculis*, or both, or a *Zanthoxylum* extract is a mixture of extracts from one, two, three, four or more *Zanthoxylum* species.

In further embodiments, a *Zanthoxylum americanum* extract or a *Zanthoxylum clava-herculis* extract is enriched for one or more isoquinoline alkaloids, such as magnoflorine, laurifoline, or both. In still further embodiments, a *Zanthoxylum* extract enriched for magnoflorine, laurifoline, or both is a combination of extracts from one, two, three, four or more *Zanthoxylum* species. In yet further embodiments, there is provided isolated, partially purified, or substantially purified magnoflorine, laurifoline, or both from a *Zanthoxylum* extract. In certain embodiments, a *Zanthoxylum* extract enriched for isoquinoline alkaloids contains at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, or at least about 15% isoquinoline alkaloids. In other embodiments, a *Zanthoxylum* extract enriched for acetogenins contains from about 0.5% to about 15%, or from about 1% to about 10%, or from about 2% to about 8%, or from about 3% to about 5% isoquinoline alkaloids.

The bioactive phenolic diterpenes of this disclosure may be obtained by synthetic methods or extracted from one or more plants, such as *Rosmarinus, Salvia*, or both. In certain embodiments, a Rosemary extract is from *Rosmarinus officinalis*, or a Rosemary extract is a mixture of extracts from one, two, three, or four *Rosmarinus* species. In certain other embodiments, a *Salvia* extract is from *Salvia officinalis*, or a *Salvia* extract is a mixture of extracts from one, two, three, or four *Salvia* species.

In further embodiments, a *Rosmarinus officinalis* extract or a *Salvia officinalis* extract is enriched for terpenoids, such as carnosic acid, carnosol, ursolic acid, or any combination thereof. In still further embodiments, an extract enriched for carnosic acid, carnosol, ursolic acid, or any combination thereof is a combination of *Rosmarinus* and *Salvia* extracts, a combination of *Rosmarinus officinalis* and *Salvia officinalis* extracts, or a combination of extracts from one, two, three, or four *Rosmarinus* species and one, two, three, or four *Salvia* species. In yet further embodiments, there is provided isolated, partially purified, or substantially purified carnosic acid from a *Rosmarinus* extract, a *Salvia* extract, or both. In certain embodiments, a *Rosmarinus* extract or a *Salvia* extract enriched for carnosic acid contains at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 71%, at least about 72%, at least about 73%, at least about 74%, at least about 75%, at least about 76%, at least about 77%, at least about 78%, at least about 79%, or at least about 80% carnosic acid. In other embodiments, a *Rosmarinus* extract or a *Salvia* extract enriched for carnosic acid contains from about 25% to about 80%, or from about 30% to about 75%, or from about 30% to about 60%, or from about 71% to about 77% carnosic acid.

In certain embodiments, the instant disclosure provides a composition comprising an *Annona* extract, such as an *Annona* fruit extract. In further embodiments, an *Annona* extract is enriched for one or more acetogenins.

In certain embodiments, the instant disclosure provides a composition comprising a mixture of an *Annona* extract and a *Zanthoxylum* extract, such as an *Annona* extract enriched for one or more acetogenins, a *Zanthoxylum* extract enriched for one or more isoquinoline alkaloids, or an *Annona* extract enriched for one or more acetogenins and a *Zanthoxylum* extract enriched for one or more isoquinoline alkaloids. In further embodiments, the *Annona* extract is an *Annona squamosa* extract, the *Zanthoxylum* extract is a *Zanthoxylum americanum* extract, a *Zanthoxylum clava-herculis* extract, or a combination thereof, or the *Annona* extract is an *Annona squamosa* extract and the *Zanthoxylum* extract is a *Zanthoxylum americanum* extract, a *Zanthoxylum clava-herculis* extract, or a combination thereof. In some embodiments, the *Annona* extract is an *Annona* fruit extract, the *Zanthoxylum* extract is a *Zanthoxylum* bark extract, or the the *Annona* extract is an *Annona* fruit extract and the *Zanthoxylum* extract is a *Zanthoxylum* bark extract. In certain embodiments, the *Annona* extract is enriched for squamocin, motrilin, or both. In other embodiments, the *Zanthoxylum* extract is enriched for one or more aporphine alkaloids, such as magnoflorine, lauriflorine, or both.

In further embodiments, any of the aforementioned compositions further comprise a Rosemary extract, such as a Rosemary extract enriched for terpenes. In yet further embodiments, the added Rosemary extract is from *Rosmarinus officinalis*, *Rosmarinus tomentosus*, *Rosmarinus eriocalyx*, *Rosmarinus palaui*, or any combination thereof. In still further embodiments, the Rosemary extract enriched for terpenes comprises carnosic acid, carnosol, ursolic acid, or any combination thereof. In any of the aforementioned embodiments, one, two or all extracts are decolorized.

In certain embodiments, the instant disclosure provides a composition comprising a mixture of an *Annona* extract and a Rosemary extract, such as an *Annona* extract is enriched for one or more acetogenins, a Rosemary extract is enriched for one or more terpenes (such as phenolic diterpenes), or an *Annona* extract is enriched for one or more acetogenins and a Rosemary extract is enriched for one or more terpenes (such as phenolic diterpenes). In further embodiments, the *Annona* extract is an *Annona squamosa* extract, the Rosemary extract is from *Rosmarinus officinalis*, *Rosmarinus tomentosus*, *Rosmarinus eriocalyx*, *Rosmarinus palaui*, or any combination thereof, or the the *Annona* extract is an *Annona squamosa* extract and the Rosemary extract is from *Rosmarinus officinalis*. In some embodiments, the *Annona* extract is an *Annona* fruit extract, the Rosemary extract is a *Rosmarinus* leaf extract, or the *Annona* extract is an *Annona squamosa* fruit extract and the Rosemary extract is a *Rosmarinus officinalis* leaf extract. In certain embodiments, the *Annona* extract is enriched for squamocin, motrilin, or both. In other embodiments, the Rosemary is enriched for one or more phenolic diterpenes, such as carnosoic acid, carnosol, or both. In any of the aforementioned embodiments, one or both extracts are decolorized.

For the purposes of administration, the compounds of the present disclosure may be administered as a raw chemical (e.g., plant extract) or may be formulated as pharmaceutical or dermatological or cosmetic compositions. In certain embodiments, pharmaceutical or dermatological or cosmetic compositions of the present disclosure comprise any one or more of the compounds having structure (I) to (V) and a pharmaceutically or dermatologically or cosmetically acceptable carrier, diluent or excipient. The compounds of structures (I) to (V) are individually or in combination present in the composition in an amount that is effective to treat a particular disease or condition of interest—that is, in an amount sufficient for skin care, to manage or control or reduce or prevent cellulite, inhibit cellulite formation, reduce visible fat deposits in cutaneous tissue, tighten and firm sagging or loose skin, manage or control or reduce or prevente the effect of skin aging (anti-aging), manage or control or reduce or prevent age spots, improve skin tone, improve skin elasticity, reduce water retention for smoother and tighter skin, smooth and tone skin, promote skin rejuvenation, control or reduce bruises/bruising, protect against free radical damage, manage or control or reduce stretch marks, reduce fat synthesis, reduce fat content in cells (e.g., adipocytes), reduce fat cells, reduces cell differentiation into fat cells, promote lipolysis, improve fat removal, maintain or promote or support a healthy lipid profile, maintain or promote or support healthy cholesterol level, promote weight loss, reduce body mass index (BMI), manage or reduce thigh or arm circumference, reduce double chin, reduce or manage or control periorbital puffiness or subor-bicularis oculi fat or eye bags, promote weight control, support weight management, promote collagen synthesis, promote hyaluronic acid synthesis, improve or activate (cutaneous) microcirculation, maintain or support cardiovascular function, support immune system to inhibit or reduce (visible) fat deposit formation in cutaneous tissue, maintain or promote or support healthy blood sugar level to inhibit or reduce (visible) fat deposit formation in cutaneous tissue, or any combination thereof; or any other associated indication described herein, and generally with an acceptable safety profiel for the subject being treated. Promoting, managing, or improving skin health or any of the aforementioned conditions by compounds set forth in any one of structures (I) to (V) can be determined by one skilled in the art, for example, as described in the Examples below. Appropriate concentrations and dosages can be readily determined by one skilled in the art.

Administration of the compounds of this disclosure, or their pharmaceutically or dermatologically or cosmetically acceptable salts, in isolated or pure form or in an appropriate pharmaceutical or dermatological or cosmetic composition, can be carried out using any accepted mode of administration for agents serving similar utilities. Pharmaceutical or dermatological or cosmetic compositions of this disclosure are formulated so as to allow the active ingredients contained therein to be bioavailable upon administration of the composition to a patient.

The compositions may be administered to a subject as a single dosage unit (e.g., a powder, liquid, or gel), or the compositions may be administered as a plurality of dosage units (e.g., in aerosol form). For example, an anti-cellulite, body slimming or skin care formulation of this disclosure may be sterilized and packaged in single-use, plastic laminated pouches or plastic tubes of dimensions selected to provide for routine, measured dispensing. In some examples, a container may have dimensions anticipated to dispense 0.5 ml of an anti cellulite, body slimming or skin care formulation (e.g., a cream, lotion, gel form) to a limited area of the target surface on a subject to treat or prevent disorders that affect skin appearance (such as cellulite, aging, weathering, being overweight, or the like). An exemplary target is in the immediate vicinity of the skin disorder, such as the face (e.g., periorbital puffiness, suborbicularis oculi fat, eye bags), chin/neck area (e.g., double chin), thighs, hips, and abdomen. The thighs, hips, and abdomen are where, for example, cellulite may be visible or where there is a risk for cellulite formation.

Pharmaceutical or dermatological or cosmetic compositions of this disclosure can be prepared by combining a compound or extract of this disclosure with an appropriate pharmaceutically or dermatologically or cosmetically acceptable carrier, diluent or excipient, and may be formulated into preparations in solid, semi-solid, liquid, semi-liquid, suspension, emulsion, gel, or gaseous forms, including powders, granules, microspheres, or aerosols (see *Remington: The Science and Practice of Pharmacy*, 20th Edition, Philadelphia College of Pharmacy and Science, 2000). In one aspect, carrier(s) are particulate so that the compositions are, for example, in powder form. Carrier(s) may be liquid, with the compositions being, for example, an ointment, cream, or an aerosol. In certain embodiments, the compounds and compositions of this disclosure are administered topically and not orally or parentarelly. Topical administration refers to any route of administration through the skin, including creams, lotions, ointments, gels, emulsions, patches, sprays, or the like.

Compositions may contain one or more inert diluents, carriers or excipients, including binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, sodium starch glycolate, corn starch or the like; lubricants such as magnesium stearate or hydrogenated soybean oil; glidants such as colloidal silicon dioxide; fragrance enhancing agents; coloring agents; or any combination thereof. Such compositions may further include one or more of a surfactant, preservative, wetting agent, dispersing agent, suspending agent, buffer, stabilizer or isotonic agent. In addition, such compositions may also contain, in addition to materials of the above type, a carrier such as polyethylene glycol or oil.

A liquid pharmaceutical or dermatological or cosmetic compositions of this disclosure, whether they be solutions, suspensions or other like form, may include one or more of the following additives: sterile diluents such as water, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as ethanol, benzyl alcohol, methyl paraben or ntural preservatives; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose.

Pharmaceutical or dermatological or cosmetic compositions of this disclosure are intended for topical administration, wherein a carrier may suitably comprise a solution, emulsion, cream, lotion, ointment, or gel base. The base, for example, may comprise one or more of the following: petrolatum, lanolin, cocoa butter, polyethylene glycols, bee wax, mineral oil, diluents such as water or alcohol, or emulsifiers or stabilizers. Thickening agents may be present in a pharmaceutical or dermatological or cosmetic composition for topical administration. If intended for transdermal administration, the composition may include a transdermal patch or iontophoresis device.

The pharmaceutical or dermatological or cosmetic composition of this disclosure in solid or liquid form may include an agent that binds to or associates with the compound of this disclosure and thereby assists in the delivery of the compound. Suitable agents that may act in this capacity include a monoclonal or polyclonal antibody, a protein or a liposome.

The pharmaceutical or dermatological or cosmetic composition of this disclosure in solid or liquid form may include reducing the size of a particle to, for example, improve bioavailability. The size of a powder, granule, particle, microsphere, or the like in a composition, with or without an excipient, can be macro (e.g., visible to the eye or at least 100 µm in size), micro (e.g., may range from about 100 µm to about 100 nm in size), nano (e.g., may no more than 100 nm in size), or any size in between, or any combination thereof to improve size and bulk density.

The pharmaceutical or dermatological or cosmetic composition of this disclosure may consist of dosage units that can be administered or applied as an aerosol or spray. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, or the like, which together may form a kit. One skilled in the art, without undue experimentation, may determine the most appropriate aerosol(s) or other delivery device.

The pharmaceutical or dermatological or cosmetic compositions of this disclosure may be prepared by methodology well known in the pharmaceutical or dermatological or cosmetic art. For example, a pharmaceutical or dermatological or cosmetic composition to be administered topically can be prepared by combining a compound of this disclosure with water (e.g., sterile, distilled) so as to form a solution. A surfactant may be added to facilitate the formation of a homogeneous solution or suspension. Surfactants are agents that non-covalently interact with compounds of this disclosure so as to facilitate dissolution or homogeneous suspension of the compound in an aqueous delivery system.

The compounds of this disclosure, or their pharmaceutically or dermatologically acceptable salts, are administered in a therapeutically effective amount, which will vary depending upon a variety of factors including the activity of the specific compound employed; the stability and length of action of the compound; the age, body weight, general health, sex, or diet of a subject; the mode or time of administration; the drug combination; the severity of the particular disorder or condition; and the subject undergoing therapy.

Compounds of this disclosure, or pharmaceutically or dermatologically or cosmetically acceptable derivatives thereof, may also be administered simultaneously with, prior to, or after administration of one or more other therapeutic or bioactive agents. In certain embodiments, such a combination therapy may include topical administration of a single pharmaceutical or dermatological or cosmetic formulation that contains compounds or compositions of this disclosure together with one or more additional active agents. In other embodiments, a combination therapy may comprise topical administration of compounds or compositions of this disclosure and administration by any route of each additional active agent in its own separate pharmaceutical or dermatological or cosmetic formulation. For example, compounds or compositions of this disclosure and another active agent can be administered to the patient together in a single liquid, gel, cream, lotion or ointment formulation. Alternatively, compounds or compositions of this disclosure are administered topically while additional bioactive agents are administered in a separate, for example, oral dosage formulation. Where separate dosage formulations are used, compounds or compositions of this disclosure and one or more additional active agents can be administered at essentially the same time, i.e., concurrently, or at separately staggered times, i.e., sequentially; combination therapy is understood to include all these regimens.

In certain embodiments, the instant disclosure provides compositions comprising a mixture of an *Annona* extract enriched for one or more major active ingredients (e.g., acetogenins, such as squamosin, motrilin) and a *Zanthoxylum* extract enriched for one or more major active ingredients (e.g., isoquinoline alkaloids, such as magnoflorine, laurifoline). In certain embodiments, an *Annona* extract is enriched for squamosin, motrilin, or both, and a *Zanthoxylum* extract is enriched for magnoflorine, laurifoline, or both. In further embodiments, a pharmaceutical or dermatological or cosmetic formulation comprising an extract mixture as described herein comprises from about 0.01 weight percent (wt %) to about 5.0 wt % or about 0.1 weight percent (wt %) to about 1.0 wt % of the major active ingredients in an *Annona* extract, such as squamosin, motrilin, or both. In yet further embodiments, a pharmaceutical or dermatological or cosmetic formulation comprising an extract mixture as described herein comprises from about 0.5 wt % to about 10 wt % of the major active ingredients in a *Zanthoxylum* extract, such as magnoflorine, laurifoline, or both. In other embodiments, a pharmaceutical or dermatological or cosmetic formulation made up of any of the aforementioned extract mixtures comprises the *Annona* and *Zanthoxylum* extracts blended in about a 1:2 to about a 1:150 weight ratio, respectively. In any of the aforementioned compositons, one or both of the *Annona* and *Zanthoxylum* extracts are decolorized.

In any of the aforementioned exemplary compositions comprising an extract mixture, one extract included in the compositions is a Rosemary extract enriched for one or more major active ingredients, which may be optionally decolorized. In certain embodiments, a Rosemary extract is enriched for carnosoic acid, carnosol, ursolic acid, or any combination thereof. In further embodiments, a pharmaceutical or dermatological or cosmetic formulation comprising an extract mixture as described herein comprises from about 0.05 weight percent (wt %) to about 10 wt % of the major active ingredients in a *Rosmarinus* extract or a *Salvia* extract, such as carnosoic acid, carnosol, ursolic acid, or any combination thereof. In other embodiments, a pharmaceutical or dermatological or cosmetic formulation made up of an extract mixture as described herein comprises from about 0.1 wt % to about 2 wt % carnosoic acid from a Rosemary extract. In any of the aforementioned compositons, included is a decolorized Rosemary extract.

Any of the aforementioned pharmaceutical, dermatological or cosmetic extract mixture formulations comprise from about 0.5 weight percent (wt %) to about 90 wt % of total active ingredients. In certain embodiments, a pharmaceutical, dermatological or cosmetic formulation comprises from about 0.05 wt % to about 1.0 wt % *Annona* extract, from about 0.8 wt % to about 8 wt % *Zanthoxylum* extract, and from about 0.05 wt % to about 5 wt % Rosemary extract, optionally one or more extract is decolorized. In certain other embodiments, a pharmaceutical, dermatological or cosmetic formulation comprises from about 0.05 wt % to about 0.5 wt % *Annona* extract comprising about 1.0 wt % acetogenins, from about 1.0 wt % to about 6.0 wt % *Zanthoxylum* extract comprising about 3.0 wt % aporphine alkaloids, and from about 0.1 wt % to about 2 wt % Rosemary extract comprising about 30 wt % to about 60 wt % carnosic acid. In further embodiments, the *Annona*, *Zanthoxylum*, and Rosemary extracts are blended in about a 5:10:1 to about a 1:120:2 weight ratio, respectively. In still further embodiments, the *Annona*, *Zanthoxylum*, and Rosemary extracts are blended in about a 1:20:2 weight ratio, respectively.

In certain embodiments, any of the aforementioned compositions and formulations of this disclosure may further comprise an adjuvant, such as a contouring agent, a skin toner, a lipolysis promoting agent, a circulation improving agent, or any combination thereof. For example, a contouring agent may be collagen, elastin, or both. In other embodiments, an adjuvant is a the skin toner, such as sacred lotus extract, celosia cristata, baccharis, aquatic mint, Chinese black tea, lycopene, hyaluronic acid, lemon, lemon essential oil, lemon essential oil combined with caffeine, salicylic acid, essential oils of juniper berries, geranium, rosemary, kola aut, caffeine, bladderwrack marine algae, punica granatum, DMAE (dimethylaminoethanol), levan molecules, avocado seed extract, pea extract, Vitamin E, or any combination thereof. In still other embodiments, an adjuvant is a lipolysis promoting agent, such as aminophylline, sacred Lotus extract, Blue Button Flower (Scabious), geranium, cangzhu, caffeine, black tea, verbana extract, conjugated linoleic acid, lauroyl proline, quinoa extract, coenzyme A, carnitine, micropatch caffeine, TEA-hydroiodide, essential oil of lemon and lemongrass, ginger extract, Yuzu seed extract, wheat protein, methylxanthines, cyclohexyl carbamate compounds, butylene glycol, *globularia cordifolia* callus culture extract, *Zingiber zerumbet* extract, unroasted Shea butter extract, active glaucine complex, Elder extract wheat proteins alcohol free, white Willow, natural red pepper oil, seaweed essence, carbopol, tea, guarana, or any combination thereof. In yet other embodiments, an adjuvant is a circulation improving agent, such as sage extract, red algae extract, maritime pine extract, escine, ivy, ivy extract, centella, ruscus, cayenne pepper, squalene, almond protein, silicium, essential oils of immortelle, peppermint, palmarosa, capsaicin, essential oil of cypress, medium chain triglycerides (MCT), artichoke extract, pitaya extract, or any combination thereof.

In further embodiments, any of the aforementioned compositions and formulations of this disclosure may further comprise a solvent, a viscosity-increasing or thickening agent, a defoamer, an emollient, a preservative, a buffering agent, a solvent, a humectant, a preservative, a chelating agent, an oleaginous compound, an antioxidant, or any combination thereof. The function of each of these diluents, carriers or excipients is not mutually exclusive within the context of the present disclosure. For example, glycerin may be used as a solvent or as a humectant or as a viscosity-increasing agent. In certain embodiments, a formulation is a composition comprising compounds or extracts of this disclosure, a viscosity-increasing agent, and a solvent, which is useful, for example, at a target site for treating, controlling, managing, or preventing cellulite formation or promoting lipolysis, as described herein.

Solvents useful in the present compositions are well known in the art and include water, glycerin, propylene glycol, isopropanol, ethanol, and methanol. In some embodiments, the solvent is water, glycerin, propylene glycol, or any combination thereof. In other embodiments, the solvent is water or ethanol. In yet other embodiments, the solvent is at least one of water, glycerin, propylene glycol, isopropanol, ethanol, and methanol.

Another useful pharmaceutical excipient of the present disclosure are viscosity-increasing or thickening agents. Exemplary viscosity-increasing agents include dextran, polyvinylpyrrolidone, methylcellulose, carboxymethyl cellulose, hydroxyethyl cellulose, hydroxypropyl methylcellulose, and hydroxypropyl cellulose, or any combination thereof.

In certain applications, it may be desirable to maintain the pH of a composition contemplated by the present disclosure within a physiologically acceptable range and within a range that optimizes the activity of the major active ingredients therein. Accordingly, a composition may further comprise a buffering agent. In certain embodiments, the buffering agent comprises a monocarboxylate or a dicarboxylate, and more specifically may be acetate, fumarate, lactate, malonate, succinate, or tartrate.

Other optional pharmaceutically acceptable excipients are those that may, for example, aid in the administration of the formulation (e.g., anti-irritant, polymer carrier, adjuvant) or aid in protecting the integrity of the components of the formulation (e.g., anti-oxidants and preservatives). An exemplary humectant is sorbitol or the like, and a preservative may be benzoic acid, benzyl alcohol, phenoxyethanol, methylparaben, propylparaben, or the like.

To form an ointment, an oleaginous compound may be used. For example, an oleaginous compound may be petrolatum. In certain other embodiments, a composition or formulation may further comprise at least one emollient. Exemplary emollients include mineral oil, cetostearyl alcohol, glyceryl stearate, or any combination thereof. In another aspect, a composition may be in the form of a semi-solid emulsion (e.g., a cream) comprising compounds or extracts of this disclosure (preferably in an amount sufficient to treat or prevent a skin condition), a solvent, a buffering agent, at least one emollient, and at least one emulsifier. In other embodiments, a semi-solid emulsion or cream may further comprise at least one of a humectant (e.g., sorbitol and/or glycerin), an oleaginous compound (e.g., petrolatum), a viscosity increasing agent (e.g., dextran, $C_{12-15}$ alkyl benzoate, polyvinylpyrrolidone, hydroxyethyl cellulose, hydroxypropyl methylcellulose, an inverse emulsion of polyacrylamide and $C_{13-14}$ isoparaffin and laureth-7), an anti-oxidant (e.g., butylated hydroxytoluene and preferably at a concentration ranging from about 0.01% to about 0.1%), a preservative (natural or synthetic or both, e.g., benzoic acid, benzyl alcohol, phenoxyethanol, methylparaben, propylparaben, potassium sorbate, benzoin powder, cinnamon, citric acid powder, grapefruit seed extract, goldenseal root extract, green tea extract, Rosemary extract, Rosemary oil extract, geranium essential oil, tea tree essential oil, neem seed essential oil, thyme essential oil, Vitamin E, Vitamin C or any combination thereof), a preservative (e.g., or any combination thereof) or natural and synthetic preservatives; or any combination thereof. In certain embodiments, an emollient (non-toxic, non-irritating, non-sensitizing, non-comedogenic) may be one or more of $C_{12-15}$ alkyl benzoate, stearyl alcohol, cetyl alcohol, or mineral oil. In certain other embodiments, the emulsifiers may be one or more of stearyl alcohol, cetyl alcohol, polyoxyethylene 40 stearate, and glyceryl monostearate.

An anti-cellulite, body slimming or skin care formulation of this disclosure may be provided in various forms, depending on the amount and number of different pharmaceutically acceptable excipients present. For example, an anti-cellulite composition may be in the form of a solid, a semi-solid, a liquid, a lotion, a cream, an ointment, a cement, a paste, a gel, or an aerosol. In certain preferred embodiments, any of the aforementioned anti-cellulite compositions and formulations, as described herein, are formulated for topical application to a target site on a subject in need thereof, such as an animal or a human. In some embodiments, an anti-cellulite composition is formulated as a powder, liquid, gel, emulsion, cream, or lotion. In other examples, a skin care composition may be in the form of a solid, a semi-solid, a liquid, a lotion, a cream, an ointment, a cement, a paste, a gel, or an aerosol. In certain preferred embodiments, any of the aforementioned skin care compositions and formulations, as described herein, are formulated for topical application to a target site on a subject in need thereof, such as an animal or a human. In some embodiments, a skin care composition is formulated as a powder, liquid, gel, emulsion, cream, or lotion. In still other examples, a body slimming composition may be in the form of a solid, a semi-solid, a liquid, a lotion, a cream, an ointment, a cement, a paste, a gel, or an aerosol. In certain preferred embodiments, any of the aforementioned body slimming compositions and formulations, as described herein, are formulated for topical application to a target site on a subject in need thereof, such as an animal or a human. In some embodiments, a body slimming composition is formulated as a powder, liquid, gel, emulsion, cream, or lotion.

Any of the aforementioned compounds, mixtures, compositions and formulations may be used for skin care, to manage or control or reduce or prevent cellulite, inhibit cellulite formation, reduce (visible) fat deposits in cutaneous tissue, tighten and firm sagging or loose skin, manage or control or reduce or prevent the effect of skin aging (anti-aging), manage or control or reduce or prevent age spots, improve skin tone, improve skin elasticity, reduce water retention for smoother and tighter skin, smooth and tone skin, promote skin rejuvenation, control or reduce bruises/bruising, protect against free radical damage, manage or control or reduce stretch marks, reduce fat synthesis, reduce fat content in cells (e.g., adipocytes), reduce fat cells, reduces cell differentiation into fat cells, promote lipolysis, improve fat removal, maintain or promote or support a healthy lipid profile, maintain or promote or support healthy cholesterol level, promote weight loss, reduce body mass index (BMI), manage or reduce thigh or arm circumference, reduce double chin, reduce or manage or control periorbital puffiness or suborbicularis oculi fat or eye bags, promote weight control, support weight management, promote collagen synthesis, promote hyaluronic acid synthesis, improve or activate (cutaneous) microcirculation, maintain or support cardiovascular function, support immune system to inhibit or reduce (visible) fat deposit formation in cutaneous tissue, maintain or promote or support healthy blood sugar level to inhibit or reduce (visible) fat deposit formation in cutaneous tissue, or any combination thereof.

EXAMPLES

Example 1

Preparation of Ethyl Acetate Extract of *Annona squamosa*

*Annona squamosa* whole fruit was dried and ground to a particle size of no larger than two millimeters (mm). Dried ground plant material (100 grams (g) was then transferred to an Erlenmeyer flask and ethyl acetate (700 milliliters (mL)) was added. The mixture was shaken for four hours, filtered and the biomass was extracted again with ethyl acetate (700 mL) for four hours. These extraction solutions were combined and evaporated under vacuum to provide 6.59 g of *Annona squamosa* ethyl acetate extract AS-EA1. The extraction yield was about 6.5% (w/w).

Example 2

Preparation of Hexane Extract of *Annona squamosa*

*Annona squamosa* dried whole fruit was ground to a particle size of no larger than two millimeters. Dried ground plant material (100 g) was then transferred to an Erlenmeyer flask and hexane (700 mL) was added. The mixture was shaken for four hours, filtered and the biomass was extracted again with hexane (700 mL) for four hours. These extract solutions were combined and evaporated under vacuum to provide 5.73 g of *Annona squamosa* hexane extract AS-HX2. The extraction yield was about 5.7% (w/w).

Example 3

Preparation of Ethanol Extract of *Annona squamosa*

*Annona squamosa* dried whole fruit was ground to a particle size of no larger than two millimeters. Dried ground plant material (100 g) was then transferred to an Erlenmeyer flask and ethanol (700 mL) was added. The mixture was shaken for four hours, filtered, and the biomass extracted again with ethanol (700 mL) for four hours. These extract solutions were combined and evaporated under vacuum to provide 26.2 g of *Annona squamosa* ethanol extract AS-EE3. The extraction yield was about 26.2% (w/w).

Example 4

Preparation of 70% EtOH Extract of *Annona squamosa*

*Annona squamosa* whole fruit was dried and ground to a particle size of no larger than two millimeters. Dried ground plant material (100 g) was then transferred to an Erlenmeyer flask and 70% ethanol (700 mL) was added. The mixture was shaken for four hours, filtered and the biomass was extracted again with 70% ethanol (700 mL) for four hours. These extract solutions were combined and evaporated under vacuum to provide 35.2 g of *Annona squamosa* 70% ethanol extract AS-EE4. The extraction yield was about 35.1% (w/w).

Example 5

Isolation of Squamocin From *Annona squamosa* Extracts

A total of 1 g of *Annona squamosa* (sugar apple) AS-EA1 extract precipitate was dissolved in methanol and then sonicated for 20 minutes. The suspension was centrifuged at 13,000 rpm for 1 minute to remove the oil fraction. The methanol soluble fraction was filtered with a 0.45 μm PTFE syringe filter and the filtrate was subjected to a RP-HPLC column (YMC-ODS) 5 μm, C18 (250×30 mm) by injection on a preparative HPLC system (JAI, LC-9104, Japan) eluted with 80% acetonitrile in $H_2O$ in 20.9 min with a UV wavelength of 210 nm, which yielded 19 mg of compound SA1 (squamocin).

Compound SA1 (Squamocin, $C_{37}H_{66}O_7$): APCI-MS (m/z) $[M+H]^+$ 623.57; UV $\lambda_{max}$ (MeOH): 262.0 nm, 301.2 nm; $^{13}C$ NMR (125 MHz, Methanol-$d_4$) δ ppm 173.94 (C-1), 134.33 (C-2), 25.18 (C-3), 27.40 (C-4), 29.18 (C-5), 29.39 (C-6), 29.61 (C-7,8,9), 29.52 (C-10), 29.31 (C-11), 29.18 (C-12), 26.66 (C-13), 33.24 (C-14), 74.19 (C-15), 84.35 (C-16), 28.95 (C-17), 28.48 (C-18), 82.83 (C-19), 82.56 (C-20), 24.80 (C-21), 28.95 (C-22), 82.21 (C-23), 71.40 (C-24), 32.46 (C-25), 22.05 (C-26), 37.49 (C-27), 71.77 (C-28), 37.27 (C-29), 25.66 (C-30), 29.76 (C-31), 31.86 (C-32), 22.63 (C-33), 14.10 (C-34), 148.89 (C-35), 77.43 (C-36), 19.22 (C-37)

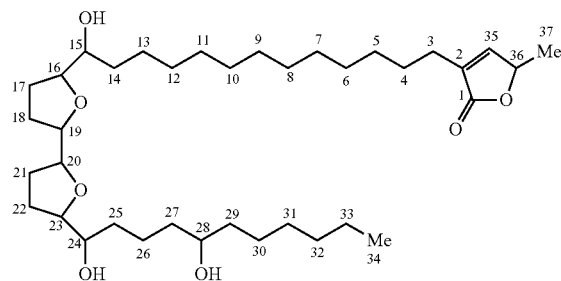

Structure of compound SA1 (Squamocin)

Example 6

Isolation Kaurenoic Acid from *Annona squamosa* Extract

A total of 2 g of decolorized *Annona squamosa* (sugar apple) extract was dissolved in methanol and then sonicated for 20 minutes. The suspension was centrifuged at 13,000 rpm for 1 minute to remove the oil, then the methanol soluble portion was filtered using a 0.45 μm PTFE syringe filter and the filtrate was subjected to a RP-HPLC column (YMC-ODS) 5 μm, $C_{18}$ (250×30 mm) by injections on a preparative HPLC system (JAI, LC-9104, Japan) eluted with 85% acetonitrile in $H_2O$ in 10 min with UV wavelength 200 nm to afford 260 mg of compound SA2 (kaurenoic acid).

Compound SA2 (kaurenoic acid, $C_{20}H_{30}O_2$): APCI-MS (m/z) [M−H]$^+$ 301.57; $^{13}C$ NMR (125 MHz, Methanol-$d_4$) δ ppm 16.5 (C-20), 19.6 (C-11), 20.5 (C-2), 23.3 (C-6), 29.7 (C-18), 34.4 (C-12), 39.4 (C-3), 40.9 (C-14), 41.0 (C-10), 42.2 (C-1), 42.7 (C-7), 44.8 (C-4), 45.4 (C-13), 45.6 (C-8), 50.3 (C-15), 56.7 (C-9), 58.4 (C-5), 103.8 (C-17), 157.0 (C-16), 181.8 (C-19, C=O)

Structure of Compound SA2 (Kaurenoic acid)

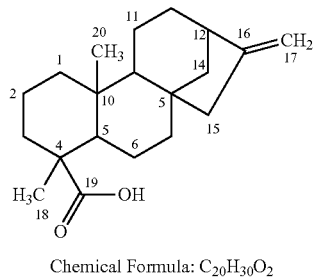

Chemical Formula: $C_{20}H_{30}O_2$

Example 7

HPLC Quantification of SA1 and SA2 in *Annona squamosa* Fractions

The identified components—Squamocin (SA1) and Kaurenoic acid (SA2)—in the *Annona squamosa* extracts were quantified using a Luna C-18 reversed-phase column (Phenomenex, 10 μm, 250 mm×4.6 mm) in an Agilent HPLC system at 210 nm. The column was eluted with a binary gradient of water (mobile phase A) and acetonitrile (mobile phase B) at 1 ml/min flow rate and 35° C. column temperature.

TABLE 1

Gradient Table of HPLC Analytical Method

| Time (min) | Mobile phase A | Mobile phase B |
|---|---|---|
| 0.0 | 30 | 70 |
| 20 | 0 | 100 |
| 23 | 0 | 100 |
| 24 | 30 | 70 |
| 30 | 30 | 70 |

Standard material kaurenoic acid (purity 100%, KFDA) and purified SA1 (Squamocin) were utilized as the quantification standard. All extract samples were prepared at a concentration of about 2 mg/ml in MeOH. After sonicating for approximately 20 minutes, the sample solution was cooled in a flask to room temperature, filtered through a 0.22 μm nylon syringe filter, and then 10 μl of the sample was injected into the column.

Example 8

Preparation of EtOAC Extract of *Annona*

*Annona squamosa* dried whole fruit was ground to a particle size of no larger than two millimeters. Dried ground plant material (2 kg) was transferred to an Erlenmeyer flask and then 14 L of ethyl acetate (EtOAc) was added. The mixture was shaken for four hours, filtered and the biomass was extracted again with 7 L EtOAc for an additional two hours. These extract solutions were combined and evaporated under vacuum to provide initial ethyl acetate extracts. These initial EtOAc extracts were a yellow viscous liquid, which formed a precipitate layer after storage at room temperature. The supernatants and precipitates of the EtOAc extracts were separated by centrifugation. Table 2 summarizes the four batches of EtOAc extraction results.

TABLE 2

Quantification of *Annona squamosa* Active Compounds in EtOAc Extracts

| | Extraction | | | Centrifugation | | |
|---|---|---|---|---|---|---|
| Extract | Raw material | Yield % | Sample | Yield (g) | Yield % | % Squamocin |
| AS-EA8 | 2 kg | 6.8 | AS-EA8S | 114 | 6.2 | 1.04 |
| | | | AS-EA8P | 6.8 | 0.4 | 11.95 |
| AS-EA8.1 | 2 kg | 6.2 | AS-EA8.1S | 109.5 | 5.5 | 1.04 |
| | | | AS-EA8.1P | 10.3 | 0.5 | 7.12 |
| AS-EA8.2 | 2 kg | 6.5 | AS-EA8.2S | 116.6 | 5.8 | 1.13 |
| | | | AS-EA8.2P | 10 | 0.5 | 12.16 |
| AS-EA8.3 | 2 kg | 6.6 | AS-EA8.3S | 118 | 5.9 | 1.08 |
| | | | AS-EA8.3P | 13 | 0.7 | 10.93 |
| Average | | 6.5 | Supernatant (S) | | 5.90 | 1.07 |
| | | | Precipitate (P) | | 0.51 | 10.54 |

The supernatants from ethyl acetate extracts had yields of 6.2% (AS-EA8S), 5.5% (AS-EA8.1S), 5.8% (AS-EA8.2S) and 5.9% (AS-EA8.3S). While the precipitates had lower yields (0.4-0.7%), they contained a much higher amount of the squamocin.

Example 9

Preparation of Supercritical Fluid $CO_2$ Extract from *Annona*

*Annona squamosa* dried whole fruit was ground to a particle size of no larger than two millimeters. Dried ground plant material (100 kg) was then transferred to a supercritical fluid extractor (pressure 25 MPa, temperature 50° C., $CO_2$ flow 70 mL/minute, two hours) and ethyl alcohol (95% food grade ethanol, quantity is 30% of raw material) was added. The supercritical fluid $CO_2$ extracts were evaporated under vacuum. Table 3 lists the extraction results from five different batch experiments.

TABLE 3

Quantification of Active Compounds from *Annona squamosa* $CO_2$ Extracts

| Extract | Raw Material (kg) | Yield % | % Squamocin | % Kaurenoic acid |
|---|---|---|---|---|
| AS-SC1 | 8.0 | 3.73 | 0.89 | 2.46 |
| AS-SC2 | 17.6 | 2.93 | 1.28 | 4.98 |
| AS-SC3 | 17.6 | 3.55 | 1.25 | 5.15 |
| AS-SC4 | 15.4 | 4.54 | 0.65 | 4.55 |
| AS-SC5 | 40 | 3.70 | 1.21 | 6.36 |

Example 10

Preparation of Decolorized *Annona* $CO_2$ Extract

A total of 250 g of *Annona squamosa* supercritical fluid $CO_2$ extract (AS-SC2) was dissolved 15-fold in ethyl acetate (3,750 mL). The suspension was agitated for 30 minutes at 180 rpm at room temperature, activated charcoal (250 g; Merck, food grade) was added, the mixture agitated for another hour, passed over filter paper (Hyundai, 285 mm), and then the filtrate was passed over a membrane filter (Whatman GF/C). The residue was extracted again with ethyl acetate (3,750 mL) for one hour, passed over filter paper and then a membrane filter. These solutions were combined and evaporated under vacuum to provide 188.9 g of decolorized *Annona squamosa* extract (AS-SCd2-EA). The decolorization yield was 75.56%.

Example 11

Quantification of Active Compounds in *Annona squamosa* EtOAc Extracts

*Annona squamosa* whole fruits were collected from different locations (noted as locations A, B, or C in Table 4) in China (CN) and India (IN). The dried fruits were ground to a particle size of no larger than two millimeters. Dried ground plant material (100 g) was placed in an Erlenmeyer flask, 700 mL ethyl acetate was added, the mixture shaken for four hours, filtered, and then the biomass was extracted again with 350 mL ethyl acetate for another two hours. These extraction solutions were combined and evaporated under vacuum to provide an ethyl acetate extract.

TABLE 4

Quantification of Active compounds in *Annona* Extract

| Extract | Collection Area | % Squamocin | % Kaurenoic acid |
| --- | --- | --- | --- |
| AS-EA8.3S | CN-A | 0.95 | 2.68 |
| AS-EA11S | CN-B | 1.21 | 4.10 |
| AS-EA11.1S | CN-B | 1.24 | 6.97 |
| AS-EA11.2S | CN-B | 1.19 | 7.10 |
| AS-EA11.3S | CN-B | 1.14 | 2.98 |
| AS-EA12S | CN-B | 1.04 | 3.86 |
| AS-EA13S | IN-A | 1.42 | 3.88 |
| AS-EA13.1S | IN-B | 0.21 | 2.72 |
| AS-EA14S | CN-A | 1.18 | 3.93 |
| AS-EA15S | IN-C | 1.13 | 5.81 |
| AS-EA15.1S | CN-A | 3.86 | 10.36 |
| AS-EA15.2S | CN-A | 3.13 | 10.88 |
| AS-EA15.3S | CN-A | 2.26 | 18.98 |
| AS-EA16S | CN-C | 0.55 | 3.65 |
| AS-EA16.1S | IN-C | 0.26 | 4.02 |

Example 12

Preparation of *Rosmarinus* (Rosemary) EtOH Extracts

*Rosmarinus officinalis* (Rosemary) dried leaf powder was extracted with ethanol or ethanol-water. The resulting solution was filtered to obtain supernatant, and subsequently was concentrated with an evaporator. Concentrated supernatant was dried under vacuum to obtain Rosemary extracts that contain from about 30% to about 60% carnosic acid.

Example 13

HPLC Quantification of Carnosic Acid in Rosemary Extracts

Carnosic acid in Rosemary leaf extracts was quantified using a Luna $C_{18}$ reversed-phase column (Phenomenex, 5 µm, 250 mm×4.6 mm) in an Agilent HPLC system and a 206 nm UV detector. The column was eluted with a binary gradient of 0.1% phosphoric acid in water (mobile phase A) and acetonitrile (mobile phase B) at 1 ml/min flow rate and 40° C. column temperature.

TABLE 5

Gradient Table of HPLC Analytical Method

| Time (min) | Mobile phase A | Mobile phase B |
| --- | --- | --- |
| 0.0 | 80 | 20 |
| 10 | 65 | 35 |
| 11 | 55 | 45 |
| 15 | 50 | 50 |
| 50 | 30 | 70 |
| 50.5 | 0 | 100 |
| 60 | 0 | 100 |
| 60.5 | 80 | 20 |
| 65 | 80 | 20 |

A commercial carnosic acid (purity 99.00%, SIGMA) was utilized as the quantification standard. All rosemary extract samples were prepared at a concentration of about 2 mg/ml in MeOH. After sonicating for approximately 20 minutes, a sample solution was cooled in a flask to room temperature, filtered through a 0.22 µm nylon syringe filter, and then 10 µl of the sample was injected into the column. Carnosic acid was identified by peak retention time and quantified based on peak area against the standard curve generated from the commercial carnosic acid.

Example 14

Preparation of Decolorized Rosemary Extract

A total of 0.5 kg of Rosemary extract containing 60% carnosic acid was dissolved in 15 times volume of methanol (7.5 L). The solution was agitated for one hour at 180 rpm at room temperature. Then 1 kg of activated charcoal (Merck, food grade) was added into the solution. The mixture was agitated for one hour, filtered with filter paper (Hyundai, 285 mm) and then filtrate was filtered with membrane filter (Whatman GF/C, cat. no. 1822 047). The residue was extracted again with methanol (7.5 L) for one hour. The solution was filtered with filter paper and then membrane filtered. These solutions were combined and evaporated under vacuum to provide 384.9 g of decolorized rosemary extract (RO-EEd12). The decolorization yield was about 74% to 76%. The same decolorization process was repeated three times.

TABLE 6

Quantification of Carnosic Acid in Decolorized *Rosemary* Extracts

| Batch No. | Extract | % Yield | % Carnosic Acid |
| --- | --- | --- | --- |
| 1 | RO-EEd12.1 | 75.8 | 71.7 |
| 2 | RO-EEd12.2 | 74.7 | 73.84 |
| 3 | RO-EEd12.3 | 74.3 | 76.7 |

The active content yields from the further decolorized rosemary extracts are provided in Table 6. As is evident, the decolorized Rosemary extracts are even further enriched for carnosic acid.

Example 15

Preparation of *Zanthoxylum* EtOH and Water Extracts

A total of 800 kg of dried *Zanthoxylum americanum* M. or *Zanthoxylum clava-herculis* L. (sugar apple) tree barks were dried, cut, crushed, and then extracted with approximately three volumes (2,400 L) 90% ethyl alcohol in water (v/v); the extraction was carried on at 90° C. for 8 hrs. The ethanol solution was filtered to obtain the supernatant, which was then concentrated with an evaporator under vacuum at 40° C. These extraction and concentration procedures were repeated three times. The final extraction solutions were then combined and concentrated together. The concentrated solution was stored for 24 hours in the refrigerator to obtain a supernatant. The supernatant was vacuum-dried to obtain 87.5 kg of *Zanthoxylum* EtOH extract powder ZA-EE15. The extraction yield was about 10.9% (w/w).

In further extracts, dried *Zanthoxylum americanum* M. tree barks were ground into powder, 20 grams of powder was mixed with enough diatomaceous earth to fill up a 100 mL extraction cell, and the extracted with 90%, 70%, 50%, 30% Ethanol/water or water alone using Accelerated Solvent Extractor (ASE) 350 (Dionex Corp., US)(e.g., the extraction conditions included heat for 5 minutes, static for 5 minutes, flush with 80 volumes, purged for 900 seconds, cycle through the process 3 times, done under pressure at 1500 psi and a temperature of 80° C.). After extraction, the solution was concentrated with an evaporator at 50° C. to produce a solid extract. The extraction yields were as follows: 90% EtOH extract, 15.5%; 70% EtOH extract, 14.7%; 50% EtOH extract, 16.8%; 30% EtOH extract, 15.7%; and Water extract, 13.9%, respectively. The total alkaloid contents containing magnoflorine and laurifoline were as follows: 90% EtOH extract, 7.1%; 70% EtOH extract, 8.6%; 50% EtOH extract, 9.6%; 30% EtOH extract, 11.2%; and Water extract, 8.0%, respectively.

Example 16

Silica Column Fractionation of *Zanthoxylum* EtOH Extracts

A total of 100.8 grams of *Z. americanum* extract ZA-EE15 (described in Example 15) was loaded onto a silica gel column and eluted with a stepwise application of solvent mixture containing linear gradient of MeOH:water (5:1 to 1:4 and 100% water) to produce nine fractions. The weight distributions are provided in Table 7.

TABLE 7

Quantity of Column fractions from *Zanthoxylum* Extract

| | Fraction | | | | | | | | |
|---|---|---|---|---|---|---|---|---|---|
| | 1 | 2 | 3 | 4 | 5 | 6 | 7 | 8 | 9 |
| Weight (g) | 35.5 | 2.4 | 1.7 | 4.3 | 2.7 | 9.8 | 3.3 | 1.5 | 33.7 |

Example 17

HPLC Quantification of Magnoflorine and Laurifoline from *Zanthoxylum* Extracts The active components magnoflorine and laurifoline in *Zanthoxylum* EtOH extracts were quantified with a Luna C18 reversed-phase column (Phenomenex, 5 µm, 250 mm×4.6 mm) in an Agilent 1200 HPLC system at 275 nm. The column was eluted with a binary gradient of water (mobile phase A) and acetonitrile (mobile phase B) at 1 ml/min flow rate and 35° C. column temperature.

TABLE 8

Gradient Table of HPLC Analytical Method

| Time (min) | Mobile phase A | Mobile phase B |
|---|---|---|
| 0.0 | 85 | 15 |
| 15 | 85 | 15 |
| 16 | 20 | 80 |
| 21 | 20 | 80 |
| 22 | 85 | 15 |
| 30 | 85 | 15 |

A commercial magnoflorin preparation (purity 99.5%, TAIJI) was utilized as the quantification standard. All extract samples were prepared in a concentration around 2 mg/ml in 0.1% AcOH:MeOH (85:15). After sonication for about 20 minutes, the sample solution was cooled in a flask to room temperature, filtered through a 0.22 um nylon syringe filter, and then 10 µl of the sample was injected into the column. Magnoflorine and laurifoline were identified by retention times of each peak in HPLC chromatogram. The quantification of magnoflorine and laurifoline were based on the peak areas calculated from standard curve of pure compound.

Example 18

Preparation of Decolorized *Zanthoxylum* Extract

A total of 1 kg *Zanthoxylum* extract generated according to Example 15 was dissolved in 15 volumes of methanol (15 L), agitated for one hour at 180 rpm at room temperature, and then 1 kg of activated charcoal (Merck, food grade) was added into suspension. The mixture was agitated for another one hour, filtered with filter paper (Hyundai, 285 mm), and then the filtrate was filtered with membrane filter (Whatman GF/C, cat. no. 1822 047). The recovered residue was extracted again with 15 L methanol for one hour, filtered with filter paper, and then with membrane filter. These solutions were combined and evaporated under vacuum to provide 0.7 kg of decolorized *Zanthoxylum* extract ZA-EEd18. The decolorization yield was 70% by weight. A total of 0.7 kg decolorized *Zanthoxylum* extract ZA-EEd18 was dissolved in around 6 L water with 1.4 kg maltodextrin in a 1:2 ratio. The suspension was dried by using spray-dryer and the yield of *Zanthoxylum* composition ZA-EEdm18.1 was 1,948 g. The spray-dry process yield was 92.8%. This process was repeated three times and the active contents in three batches of the processed *Zanthoxylum* extract are listed in Table 9.

TABLE 9

Quantification of Active Compounds in *Zanthoxylum* Compositions

| Extract | Magnoflorine + Laurifoline |
|---|---|
| ZA-EEdm18.1 | 3% |
| ZA-EEdm18.2 | 3% |
| ZA-EEdm18.3 | 3.2% |

Example 19

Measurement of Decolorization Efficiency of Rosemary Extracts

To measure the absorbance of decolorized Rosemary extract, a 1% solution in methanol was prepared and then filtered through a 0.45 μm nylon syringe filter. A 1 ml volume of solution was placed in a 1 cm quartz vessel (Bioteck biocell) and absorption at a UV wavelength of 660 nm was measured using a spectrophotometer (PowerWave XS Microplate Spectrophotometer). Efficient decolorization of a Rosemary extract was considered to be a UV 660 nm value below 0.3. The visual color appearance of the Rosemary extract powder was defined as light yellow or light greenish. Three different decolorized Rosemary extracts from Example 14 were analyzed.

TABLE 10

Absorbance Value of Decolorized Rosemary Extract (1% MeOH)

| Extract | UV 660 nm | Powder color |
|---|---|---|
| RO-EEd12.1 | 0.057 | Light yellow |
| RO-EEd12.2 | 0.05 | Light yellow |
| RO-EEd12.3 | 0.056 | Light yellow |

Example 20

Measurement of Decolorization Efficiency of Zanthoxylum Extracts

To measure the absorbance of decolorized Zanthoxylum extract, a 1% solution in 50% aqueous methanol (50% MeOH:50% H$_2$O) was prepared and then filtered through a 0.45 μm nylon syringe filter. A 1 ml volume of solution was placed in a 1 cm quartz vessel (Bioteck biocell) and absorption at a UV wavelength ranging from 450 to 900 nm was measured using a spectrophotometer (PowerWave XS Microplate Spectrophotometer), and compared to absorption of undecolorized Zanthoxylum extract. Efficient decolorization of a Zanthoxylum extract was considered to be a UV 450 nm, 550 nm, and 650 nm value below below 0.7. The visual color appearance of the Zanthoxylum extract powder was defined as light beige. Three different decolorized Zanthoxylum extracts from Example 18 were analyzed.

TABLE 11

Absorbance Value of Decolorized Zanthoxylum Composition

| Extract | Value @ 450 nm | Value @ 550 nm | Value @ 650 nm | Max Value @ 450 nm-900 nm | Powder color |
|---|---|---|---|---|---|
| ZA-EEdm18.1 | 0.37 | 0.11 | 0.06 | 0.37 | Light beige |
| ZA-EEdm18.2 | 0.42 | 0.14 | 0.08 | 0.42 | Light beige |
| ZA-EEdm18.3 | 0.39 | 0.12 | 0.07 | 0.39 | Light beige |

Example 21

Preparation of Annona:Rosemary:Zanthoxylum Blend (ARZ-21)

A blend of decolorized Annona extract, Rosemary extract, and decolorized Zanthoxylum extract was made at a ratio of 1:2:20 (w/w/w). A total of 800 g of decolorized Zanthoxylum composition ZA-EEdm18.1 was placed into a 5 L scale Ribbon-blender (Han-Seong F&C, Korea), and then 40 g of decolorized Annona extract was added by dropping. The two extracts were blended for one hour at a speed of 20 rpm agitation. Subsequently, 80 g of Rosemary extract was added to the Zanthoxylum/Annona mix and blended for an additional two hours to yield 899.4 g of final product ARZ-21 (recovery yield 97.8%). The process was repeated three times. The active contents in the ARZ-21 are listed in Table 12.

TABLE 12

Quantification of Active Contents in Three Component Product ARZ-21

| Extract | Carnosic acid + carnosol | Alkaloids | Kaurenoic acid |
|---|---|---|---|
| ARZ-21.1 | 5% | 3% | 0.5% |
| ARZ-21.2 | 5% | 3% | 0.5% |
| ARZ-21.3 | 5% | 3% | 0.5% |

Example 22

Lipid Accumulation Assay in Adipocytes

Mouse embryo fibroblast 3T3-L1 cells (purchased from American Type Culture Collection) were cultured in Dulbecco's modified Eagle's medium (DMEM) (GIBCO) containing 10% bovine calf serum until confluent. Two days post-confluence (D0), the cells were stimulated to differentiate into an adipocyte-like phenotype by adding DMEM containing 10% fetal bovine serum (FBS), 5 μg/ml insulin, 0.5 mM 3-isobutyl-1-methylxanthine (IBMX) and 1 μM dexamethasone for two days (D2). Cells were then maintained in 10% FBS/DMEM medium with 5 μg/ml insulin for another two days (D4), followed by culturing with 10% FBS/DMEM medium for four days (D8). Test samples at various concentrations were added to the cells from Day 0 to Day 8 of adipogenesis, during which the medium was exchanged every 2 days with fresh medium containing the test sample. On Day 8, lipid droplets in cells were stained with Oil red 0 (ORO) and signal measured at 510 nm.

Example 23

Effect of Annona Extracts, Fractions and Active Compounds on Lipid Accumulation

The lipid accumulation assay of Example 19 was carried out with Annona squamosa ethanol extracts AS-EE3 and AS-EE4 (as generated in Examples 3 and 4, respectively). Briefly, three concentrations of Annona AS-EE3 (100% EtOH) and AS-EE4 (70% EtOH) extracts (0.1, 0.5 and 1 μg/ml) and positive control TNF-α (10 ng/mL) were used to treat 3T3-L1 cells during the differentiation period (from Day 0 to Day 8 of adipogenesis). Cell culture medium containing extracts was changed every 2 days and ORO staining was used to detect lipid droplet accumulation in cells.

TABLE 13

Effect of Annona EtOH Extract on Lipid Accumulation

| | Inhibition (%) | | | |
|---|---|---|---|---|
| Samples | 10 ng/ml | 0.1 μg/ml | 0.5 μg/ml | 1 μg/ml |
| TNF-α | 49.2 ± 4.3 | — | — | — |
| AS-EE3 (100% EtOH) | — | 5.1 ± 10.8 | 23.5 ± 8.3 | 82.8 ± 1.5 |
| AS-EE4 (70% EtOH) | — | 0.0 ± 11.4 | 9.6 ± 9.5 | 66.1 ± 3.4 |

ORO staining showed that *Annona* extracts significantly inhibited lipid accumulation in 3T3-L1 adipocyte-like cells (Table 13). Both *Annona* extracts reduced lipid accumulation in a dose dependent manner. In fact, the AS-EE3 (100% EtOH) extract at the highest dose (1 µg/ml) almost completely inhibited lipid accumulation.

The supernatant and precipitate parts of *Annona squamosa* fruit hexane extracts (as produced in Example 2) were also tested for their effect on lipid accumulation. Three concentrations of the *Annona* hexane extracts (0.05, 0.1 and 0.5 µg/ml) were used to treat 3T3-L1 cells during the differentiation period (from Day 0 to Day 8 of adipogenesis), then stained for lipid accumulation on Day 8.

TABLE 14

Effect of *Annona* Hexane Extract on Lipid Accumulation

| | Inhibition (%) | | | |
|---|---|---|---|---|
| Samples | 10 ng/ml | 0.05 µg/ml | 0.1 µg/ml | 0.5 µg/ml |
| TNF-α | 49.2 ± 4.3 | — | — | — |
| AS-HX2.1 | — | 0.0 ± 6.5 | 0.0 ± 9.2 | 64.9 ± 4.5 |
| AS-HX2.1-Supernatant | — | 9.6 ± 5.6 | 5.5 ± 9.1 | 66.8 ± 4.2 |
| AS-HX2.1-Precipitate | — | 0.0 ± 9.1 | 8.3 ± 5.8 | 46.2 ± 6.6 |

As shown in Table 14, the hexane extract and its supernatant part exhibited high inhibition (more than 60%) at a dose of 0.5 µg/ml, while the hexane extract precipitate part at the same concentration showed 46.2% of inhibition on lipid accumulation (which was similar to the level of inhibition by the positive control, TNF-α).

Ethyl acetate extracts of *Annona squamosa* fruit and their supernatant and precipitate parts (as produced in Example 8) were also tested for their effect on lipid accumulation. Similar to the previous extracts, each EtOAc extract was tested at three doses of 0.05 µg/ml, 0.1 µg/ml and 0.5 µg/ml.

TABLE 15

Effect of *Annona* EtOAc Extract on Lipid Accumulation

| | Inhibition (%) | | | |
|---|---|---|---|---|
| Samples | 10 ng/ml | 0.05 µg/ml | 0.1 µg/ml | 0.5 µg/ml |
| TNF-α | 75.5 ± 5.2 | — | — | — |
| AS-EA8 | — | 0.0 ± 9.3 | 9.1 ± 13.3 | 78.3 ± 4.0 |
| AS-EA8-Supernatant | — | 0.0 ± 9.7 | 0.0 ± 14.8 | 51.3 ± 4.7 |
| AS-EA8-Precipitate | — | 8.7 ± 7.5 | 75.3 ± 1.4 | 74.3 ± 1.3 |

As shown in Table 15, the EtOAc extracts and its supernatant part showed 78.3% and 51.3% of inhibition, respectively, at 0.5 µg/ml. The EtOAc extract precipitate part inhibited lipid accumulation in a dose dependent manner and showed more than 70% inhibition at the lower dose of 0.1 µg/ml.

Super critical fluid $CO_2$ extracts of *Annona squamosa* fruit (as produced in Example 9) were tested for lipid accumulation. Similar to the previous extracts, each of the $CO_2$ extracts were tested at the following six doses of 0.0625 µg/ml, 0.125 µg/ml, 0.25 µg/ml, 0.35 µg/ml, 0.5 µg/ml, and 1 µg/ml.

TABLE 16

Effect of *Annona* $CO_2$ Extract on Lipid Accumulation

| Samples | Concentration | Inhibition (%) |
|---|---|---|
| TNF-α | 10 ng/ml | 44.2 ± 4.8 |
| $CO_2$ extract | 0.0625 µg/ml | 0.0 ± 11.0 |
| | 0.125 µg/ml | 0.4 ± 9.2 |
| | 0.25 µg/ml | 23.5 ± 11.7 |
| | 0.35 µg/ml | 43.0 ± 14.7 |
| | 0.5 µg/ml | 60.7 ± 4.5 |
| | 1 µg/ml | 66.8 ± 2.0 |

As shown in Table 16, the $CO_2$ extract of *Annona squamosa* reduced lipid accumulation in a dose dependent manner and showed more than 60% of reduction at a dose of 0.5 µg/ml or higher.

*Annona squamosa* fruit $CO_2$ extract and the decolorized $CO_2$ extract (as produced, for example, in Example 10) were tested for their effect on lipid accumulation at six doses, as follows: 0.0625 µg/ml, 0.125 µg/ml, 0.25 µg/ml, 0.35 µg/ml, 0.5 µg/ml and 1 µg/ml. As shown in Table 14, the $CO_2$ extract still showed good effect in a dose dependent manner, but decolorized $CO_2$ extract showed a different pattern depending on the solvent used in the decolorization process. Decolorized $CO_2$ extract using EtOAc didn't show any effect, but decolorized $CO_2$ extract using hexane showed good efficacy with dose dependent manner. The efficacy of it is similar to that of $CO_2$ extract.

TABLE 17

Effect of *Annona* Extracts on Lipid Accumulation

| | Inhibition (%) | | | | | | |
|---|---|---|---|---|---|---|---|
| | (ng/ml) | (µg/ml) | | | | | |
| Samples | 10 | 0.0625 | 0.125 | 0.25 | 0.35 | 0.5 | 1 |
| TNF-α | 77.1 ± 4.5 | — | — | — | — | — | — |
| AS-SC2 | — | 0.0 ± 11.0 | 0.4 ± 9.2 | 23.5 ± 11.7 | 43.0 ± 14.7 | 60.7 ± 4.5 | 66.8 ± 2.0 |
| AS-SCd2-EA | — | 7.9 ± 21.7 | 5.6 ± 16.6 | 0.9 ± 5.3 | 7.8 ± 14.4 | 5.0 ± 7.7 | 0.0 ± 17.9 |
| AS-SC2 | — | 5.9 ± 14.5 | 0.6 ± 13.6 | 11.9 ± 11.5 | 27.0 ± 2.7 | 52.4 ± 11.8 | 69.8 ± 6.1 |
| AS-SCd2-HX | — | 9.9 ± 1.9 | 4.2 ± 28.5 | 8.3 ± 9.2 | 32.1 ± 20.7 | 45.6 ± 2.9 | 68.8 ± 6.1 |

Two compounds, SA1 and SA2, isolated from *Annona* extracts as described in Examples 5 and 6, were tested for their effect on lipid accumulation. The active components from the *Annona squamosa* extracts were tested at five concentrations for each compound, as follows: 0.005 µg/ml, 0.01 µg/ml, 0.05 µg/ml, 0.1 µg/ml and 0.5 µg/ml.

TABLE 18

Effect of Compounds Isolated from *Annona Extract* on Lipid Accumulation

| | | | Inhibition (%) | | | |
|---|---|---|---|---|---|---|
| | (ng/ml) | | (µg/ml) | | | |
| Samples | 10 | 0.005 | 0.01 | 0.05 | 0.1 | 0.5 |
| TNF-α | 77.1 ± 4.5 | — | — | — | — | — |
| SA1 | — | 10.7 ± 10.9 | 37.8 ± 4.4 | 72.3 ± 3.1 | 71.6 ± 1.9 | 66.7 ± 4.7 |
| SA2 | — | 2.0 ± 21.9 | 0.0 ± 11.4 | 9.8 ± 13.6 | 12.6 ± 11.7 | 7.8 ± 17.1 |

As shown in Table 18, acetogenin-peak SA1 showed high efficacy in a dose dependent manner and peak SA2 show a weaker effect at the same dose.

The *Annona* hexane extract produced in Example 2 was tested to evaluate its effect on lipid accumulation. Three concentrations of hexane extract (0.1 µg/ml, 0.5 µg/ml and 1 µg/ml) were tested.

TABLE 19

Effect of *Annona* Hexane Extract on Lipid Accumulation

| Samples | Concentration | Inhibition (%) |
|---|---|---|
| TNF-α | 10 ng/ml | 49.2 ± 4.3 |
| AS-HX2 | 0.1 µg/ml | 48.8 ± 2.2 |
| | 0.5 µg/ml | 57.0 ± 6.7 |
| | 1 µg/ml | 59.2 ± 8.2 |

As shown in Table 19, the *Annona* hexane extract reduced lipid accumulation in a dose dependent manner.

Example 24

Effect of Rosemary Extracts on Lipid Accumulation

EtOH and H₂O/EtOH extracts of Rosemary were produced as described in Example 12. Each extract was tested at two doses (0.05 µg/ml and 0.1 µg/ml) to evaluate its effect on lipid accumulation.

TABLE 20

Effect of Rosemary Extract on Lipid Accumulation

| | Inhibition (%) | | |
|---|---|---|---|
| Samples | 10 ng/ml | 0.05 µg/ml | 0.1 µg/ml |
| TNF-α | 49.2 ± 4.3 | — | — |
| EtOH extract | — | 0.0 ± 1.5 | 76.1 ± 1.1 |
| Water + EtOH extract | — | 6.2 ± 3.4 | 33.1 ± 1.1 |

As shown in Table 20, the EtOH Rosemary extract, at a dose of 0.1 µg/ml, showed more than 70% inhibition of lipid accumulation, while the H₂O/EtOH Rosemary extract at the same dose also inhibited lipid accumulation, but to a lesser degree (33.1%).

Rosemary extracts enriched for carnosic acid and standardized at 30% and 60%, as well as decolorized rosemary extracts (as produced in Examples 12 and 14), were tested at five doses, as follows: 0.005 µg/ml, 0.01 µg/ml, 0.05 µg/ml, 0.1 µg/ml and 0.5 µg/ml.

TABLE 21

Effect of Rosemary Extracts on Lipid Accumulation

| | | | Inhibition (%) | | | |
|---|---|---|---|---|---|---|
| | (ng/ml) | | | (µg/ml) | | |
| Samples | 10 | 0.005 | 0.01 | 0.05 | 0.1 | 0.5 |
| TNF-α | 59.9 ± 9.8 | — | — | — | — | — |
| RO-EE12 (60%) | — | 4.2 ± 10.2 | 15.4 ± 8.2 | 17.3 ± 7.9 | 67.7 ± 10.0 | 83.0 ± 7.0 |
| RO-EE12 (30%) | — | 1.8 ± 11.3 | 4.1 ± 14.2 | 19.2 ± 7.5 | 40.0 ± 14.1 | 63.3 ± 11.5 |
| RO-EEd12 (60%) | — | 0.0 ± 10.4 | 2.8 ± 9.2 | 28.4 ± 5.9 | 63.4 ± 11.9 | 85.5 ± 1.6 |

As shown in Table 21, all extracts showed an inhibitory effect in a dose dependent manner on lipid accumulation, and 60% carnosic acid was more effective than 30% carnosic acid. In addition, the decolorized Rosemary extract (60% carnosic acid) was just as effective as the untreated extract.

Example 25

Effect of *Annona*:Rosemary Extract Combination on Lipid Accumulation

Combinations of extracts from *Annona squamosa* and carnosic acid-enriched Rosemary were made using extracts as prepared in Examples 10, 12 and 14. More specifically, Rosemary extracts containing either 30% carnosic acid or 60% carnosic acid (decolorized) were combined with

*Annona squamosa* extracts containing 2%, 1%, or 0.5% Squamocin (SA1). Four concentrations of each combination were tested for their effect on lipid accumulaton, as follows: 2.5 µg/ml, 5 µg/ml, 10 µg/ml and 15 µg/ml.

All three combinations containing Rosemary extract having 60% carnosic acid (CA) showed synergy at 2.5 µg/ml, as did the combination of 30% Carnosic acid with 2% Squamocin of *Annona squamosa* extract at 2.5 µg/ml.

TABLE 22

Effect of *Annona*:Rosemary Combinations on Lipid Accumulation

| Samples | | 10 ng/ml | 2.5 µg/ml | 5 µg/ml | 10 µg/ml | 15 µg/ml |
|---|---|---|---|---|---|---|
| | TNF-α | 59.9 ± 9.8 | — | — | — | — |
| RO-EEd12 (60%) | AS-SCd2 (2% SA1) | — | 40.6 ± 6.2 | 82.6 ± 0.9 | 92.4 ± 0.9 | 93.7 ± 0.4 |
| | AS-SCd2 (1% SA1) | — | 29.3 ± 14.6 | 75.6 ± 6.1 | 92.6 ± 0.5 | 94.8 ± 0.6 |
| | AS-SCd2 (0.5% SA1) | — | 6.6 ± 3.0 | 61.4 ± 7.7 | 90.5 ± 0.3 | 94.8 ± 0.3 |
| RO-EE12 (30%) | AS-SCd2 (2% SA1) | — | 28.1 ± 14.4 | 83.8 ± 2.7 | 91.8 ± 1.0 | 94.4 ± 0.5 |
| | AS-SCd2 (1% SA1) | — | 3.8 ± 6.8 | 52.6 ± 7.4 | 90.2 ± 0.7 | 90.4 ± 0.9 |
| | AS-SCd2 (0.5% SA1) | — | 0.0 ± 9.1 | 27.1 ± 7.0 | 87.6 ± 1.7 | 92.4 ± 0.6 |

All combinations inhibited lipid accumulation in a dose dependent manner. Almost all samples (5 out of six) inhibited lipid accumulation more than 90% at a dose of 10 µg/ml, while the inhibition greater than 90% for all samples at 15 µg/ml. The efficacy increase directly correlated with the amount of *Annona squamosa* extract in the combinations (i.e., greater efficacy with more *Annona* extract).

To determine whether this *Annona*:Rosemary combination acted synergistically to inhibit lipid accumulation, the effect of each combination was calculated using the COLBY formular for measuring synergy (Colby, *Weeds* 15:20-22, 1967). The calculated (theoretical) and actual (experimental) results are provided in Table 20.

TABLE 23

Synergy Effect of *Annona*:Rosemary Combination

| | | Inhibition (%) | | | |
|---|---|---|---|---|---|
| Samples | | 2.5 µg/ml | 5 µg/ml | 10 µg/ml | 15 µg/ml |
| 60% CA + 2% SA1 | Theoretical | 2.8 | 28.4 | 70.5 | 88.5 |
| | Result | 40.6 | 82.6 | 92.4 | 93.7 |
| 60% CA + 1% SA1 | Theoretical | 2.8 | 28.4 | 63.4 | 85.8 |
| | Result | 29.3 | 75.6 | 92.6 | 94.8 |
| 60% CA + 0.5% SA1 | Theoretical | 2.8 | 28.4 | 63.4 | 85.8 |
| | Result | 6.6 | 61.4 | 90.5 | 94.8 |
| 30% CA + 2% SA1 | Theoretical | 4.1 | 19.2 | 51.6 | 70.4 |
| | Result | 28.1 | 83.8 | 91.8 | 91.4 |
| 30% CA + 1% SA1 | Theoretical | 4.1 | 19.2 | 40.0 | 63.3 |
| | Result | 3.8 | 52.6 | 90.2 | 90.4 |
| 30% CA + 0.5% SA1 | Theoretical | 4.1 | 19.2 | 40.0 | 63.3 |
| | Result | 0 | 27.1 | 87.6 | 92.4 |

As is evident from Table 23, all combinations had unexpected synergy at doses of 5 µg/ml, 10 µg/ml and 15 µg/ml.

Example 26

Effect of *Zanthoxylum* Extracts and Fractions on Lipid Accumulation

*Zanthoxylum* 90% EtOH extract, produced as described in Example 15, was divided into a MeOH soluble fraction and a MeOH insoluble part as described in Example 16. Each extract was tested at three concentrations (20 µg/ml, 40 µg/ml, 80 µg/ml, and 160 µg/ml) to examine the effect of *Zanthoxylum* extracts on lipid accumulation.

TABLE 24

Effect of *Zanthoxylum* Extracts on Lipid Accumulation

| | Inhibition (%) | | | | |
|---|---|---|---|---|---|
| Samples | 10 ng/ml | 20 µg/ml | 40 µg/ml | 80 µg/ml | 160 µg/ml |
| TNF-α | 47.8 ± 5.5 | — | — | — | — |
| ZA-EE15 | — | — | 0.0 ± 8.0 | 35.5 ± 4.3 | 71.4 ± 0.8 |
| MeOH fraction | — | — | 30.7 ± 6.8 | 61.1 ± 1.8 | 48.8 ± 0.7 |
| Non-MeOH fraction | — | 0.0 ± 14.4 | 0.0 ± 16.9 | 0.0 ± 17.6 | — |

The *Zanthoxylum* 90% EtOH extract (ZA-EE15) and the MeOH soluble fraction inhibited lipid accumulation in a dose dependent manner, but the MeOH insoluble fraction had no detectable effect. These data indicate that the active compounds in the *Zanthoxylum* ethanol extract are MeOH soluble.

The MeOH soluble fraction from *Zanthoxylum* extract ZA-EE15 was further fractionated by the AOC fractionation method. These fractions were tested at three concentrations (20 µg/ml, 40 µg/ml, 80 µg/ml, and 160 µg/ml) to examine the effect of *Zanthoxylum* extract fractions on lipid accumulation.

TABLE 25

Effect of Zanthoxylum Extract and Fractions on Lipid Accumulation

| | Inhibition (%) | | | | |
|---|---|---|---|---|---|
| Samples | 10 ng/ml | 20 µg/ml | 40 µg/ml | 80 µg/ml | 160 µg/ml |
| TNF-α | 47.8 ± 5.5 | — | — | — | — |
| MeOH soluble part | — | — | 30.7 ± 6.8 | 61.1 ± 1.8 | 48.8 ± 0.7 |
| AOC fraction 1 | — | 68.9 ± 1.6 | 79.3 ± 1.3 | 69.1 ± 1.8 | — |
| AOC fraction 2 | — | 19.5 ± 6.6 | 65.0 ± 1.2 | 75.1 ± 1.2 | — |
| AOC fraction 3 | — | 0.0 ± 14.2 | 2.5 ± 7.6 | 9.7 ± 8.3 | — |
| AOC fraction 4 | — | 20.3 ± 15.0 | 30.7 ± 4.7 | 18.2 ± 2.0 | — |

AOC fractions 1 and 2 showed the most potent inhibitory effect on lipid accumulation and in a dose dependent manner. AOC fraction 3 had the weakest effect, while AOC fraction 4 showed about 30% inhibition.

The 90% EtOH extract from Zanthoxylum was partitioned by silica column as described in Example 16. Seven fractions were each tested at three doses (10 µg/ml, 20 µg/ml and 40 µg/ml) in the lipid accumulation assay.

TABLE 26

Effect of Zanthoxylum Extract Fractions on Lipid Accumulation

| | | Inhibition (%) | | | |
|---|---|---|---|---|---|
| Samples | | 10 ng/ml | 10 µg/ml | 20 µg/ml | 40 µg/ml |
| TNF-α | | 49.2 ± 4.3 | — | — | — |
| Zanthoxylum Silica column fractions | Fraction-2 | — | 0.0 ± 2.2 | 30.4 ± 10.1 | 56.2 ± 9.8 |
| | Fraction-3 | — | 10.7 ± 17.5 | 25.4 ± 4.3 | 49.0 ± 4.1 |
| | Fraction-4 | — | 0.0 ± 4.9 | 0.0 ± 8.4 | 9.6 ± 16.0 |
| | Fraction-5 | — | 3.8 ± 10.5 | 13.6 ± 6.3 | 20.4 ± 16.6 |
| | Fraction-6 | — | 0.0 ± 6.1 | 0.0 ± 7.2 | 0.0 ± 3.1 |
| | Fraction-7 | — | 0.0 ± 26.1 | 9.0 ± 18.0 | 19.1 ± 13.0 |
| | Fraction-8 | — | 0.0 ± 10.7 | 1.5 ± 9.2 | 16.8 ± 9.5 |

Silica column Fractions 2 and 3 were the most effective at inhibiting lipid accumulation, while fractions 5 and 7 showed about 20% of inhibition at the highest dose (40 µg/ml).

Zanthoxylum EtOH extracts (90%, 70% and 30%) and water extract were produced as described in Example 15. The four types of extracts were tested for their effect on lipid accumulation at four concentrations (20 µg/ml, 40 µg/ml, 80 µg/ml and 160 µg/ml) each.

TABLE 27

Effect of Variuos Prickly Ash Extracts on Lipid Accumulation

| | Inhibition (%) | | | | |
|---|---|---|---|---|---|
| Samples | 10 ng/ml | 20 µg/ml | 40 µg/ml | 80 µg/ml | 160 µg/ml |
| TNF-α | 37.2 ± 5.2 | — | — | — | — |
| 90% EtOH extract | — | 0.0 ± 9.0 | 14.0 ± 14.1 | 55.1 ± 6.8 | 29.0 ± 2.1 |
| 70% EtOH extract | — | 0.0 ± 6.3 | 24.6 ± 21.9 | 56.2 ± 4.2 | 39.1 ± 2.3 |
| 30% EtOH extract | — | 11.7 ± 8.5 | 15.9 ± 3.0 | 57.5 ± 5.9 | 78.4 ± 4.6 |
| Water extract | — | 25.3 ± 12.5 | 36.0 ± 7.6 | 55.0 ± 15.0 | 78.8 ± 2.9 |

As shown in Table 27, the 30% EtOH and water extracts reduced lipid accumulation in a dose dependent manner and showed a stronger inhibitory effect than others. The 90% EtOH and 70% EtOH extracts also inhibited lipid accumulation by about 50% at a dose of 80 µg/ml.

Zanthoxylum 70% EtOH extract and 30% EtOH extracts were filtered with charcoal as described in Example 18. Four concentrations (20 µg/ml, 40 µg/ml, 80 µg/ml and 160 µg/ml) of each extract were tested for their effect on lipid accumulation.

TABLE 28

Effect of Charcoal-Filtered Prickly Ash Extracts on Lipid Accumulation

| Samples | Inhibition (%) | | | | |
|---|---|---|---|---|---|
| | 10 ng/ml | 20 µg/ml | 40 µg/ml | 80 µg/ml | 160 µg/ml |
| TNF-α | 37.2 ± 5.2 | — | — | — | — |
| 70% EtOH extract | — | 0.0 ± 6.3 | 24.6 ± 21.9 | 56.2 ± 4.2 | 39.1 ± 2.3 |
| 70% EtOH extract:Charcoal = 1:3 | — | 0.0 ± 8.2 | 0.0 ± 0.4 | 23.7 ± 10.4 | 74.1 ± 5.3 |
| 30% EtOH extract | — | 11.7 ± 8.5 | 15.9 ± 3.0 | 57.5 ± 5.9 | 78.4 ± 4.6 |
| 30% EtOH extract:Charcoal | — | 0.0 ± 2.9 | 0.0 ± 13.1 | 0.0 ± 10.8 | 19.3 ± 11.5 |

Charcoal-filtered *Zanthoxylum* 70% EtOH extract caused a reduction in lipid accumulation and had a strong effect at 160 µg/ml, which was greater than the untreated *Zanthoxylum* 70% EtOH extract. Charcoal-filtered *Zanthoxylum* 30% EtOH extract showed 19.3% inhibition of lipid accumulation at 160 µg/ml.

Example 27

Effect of *Annona*:Rosemary Extract:*Zanthoxylum* Combination on Lipid Accumulation A combination of *Annona squamosal* extract AS-SCd2-EA (prepared as described in Example 10), carnosic acid-enriched Rosemary extract RO-EEd2 (prepared as described in Example 14), and *Zanthoxylum* extract ZA-EEd18 (prepared as described in Example 18) was made, and four concentrations for each individual extract and the combination, as follows: 0.9 µg/ml, 1.875 µg/ml, 3.75 µg/ml and 7.5 µg/ml; was tested in the lipid accumulation assay of Example 19.

TABLE 29

Effect of *Annona*:Carnosic Acid-Enriched Rosemary:*Zanthoxylum* Combination on Lipid Accumulation

| Sample | Treatment Dose/Inhibition (%) | | | | |
|---|---|---|---|---|---|
| TNF-α | 10 ng/ml 67.4 ± 3.16 | 0.9 µg/ml — | 1.875 µg/ml — | 3.75 µg/ml — | 7.5 µg/ml — |
| Combination | — | 0 ± 3.68 | 10.9 ± 4.66 | 47.0 ± 1.80 | 60.9 ± 8.77 |
| | — | 0.04 µg/ml | 0.08 µg/ml | 0.16 µg/ml | 0.33 µg/ml |
| *Annona* | — | 0.6 ± 5.13 | 0.0 ± 5.93 | 16.5 ± 5.72 | 35.5 ± 2.25 |
| | — | 0.08 µg/ml | 0.16 µg/ml | 0.33 µg/ml | 0.65 µg/ml |
| Rosemary | — | 2.5 ± 9.29 | 2.5 ± 4.83 | 4.9 ± 6.90 | 12.2 ± 2.64 |
| | — | 0.78 µg/ml | 1.63 µg/ml | 3.26 µg/ml | 6.52 µg/ml |
| *Zanthoxylum* | — | 3.7 ± 6.78 | 0.3 ± 7.13 | 6.6 ± 12.92 | 13.5 ± 5.63 |

Table 26 shows that the triple combination inhibited lipid accumulation in a dose dependent manner and that the efficacy of the combination is more potent than each of the individual components alone.

To determine whether this *Annona*:Carnosic Acid-Enriched Rosemary:*Zanthoxylum* combination acted synergistically to inhibit lipid accumulation, the effect of each combination was calculated using the Colby formular for measuring synergy (Colby, *Weeds* 15:20, 1967). The calculated (theoretical) and actual (experimental) results are provided in Table 27.

TABLE 30

Synergy of *Annona*:Rosemary:*Zanthoxylum* Combination

| | | Concentration (µg/ml) | | | |
|---|---|---|---|---|---|
| | | 0.9 | 1.875 | 3.75 | 7.5 |
| Combination | Theoretical inhibition (%) | 6.7 | 2.8 | 25.8 | 51.0 |
| | Experimental inhibition (%) | 0 | 10.9 | 47.0 | 60.9 |

Table 30 shows that the triple combination exhibited an unexpected synergy at inhibiting lipid accumulation when administered at the doses of 1.875 µg/ml, 3.75 µg/ml and 7.5 µg/ml as compared to the calculated additive effect of the combination.

Example 28

Differentiation Assay in Human Subcutaneous Adipocytes

The inhibition of lipid accumulation and differentiation assays examined the ability of compounds to inhibit the differentiation of human subcutaneous preadipocytes into adipocytes. Cells were grown to confluency such that all cells were synchronized and then differentiated. Cryopreserved preadipocytes were passaged with preadipocyte medium (PM-1). Cells were fed every other day with PM-1 until confluent. To induce differentiation, PM-1 medium was replaced with differentiation medium (DM-2) including insulin, dexamethasone, isobutyl methylxanthine, PPAR-γ agonist, TNF-α and test compounds at day two. After 7 days, the medium was changed to Adipocyte medium without the test compounds. On day 16 of the assay, cytotoxicity and lipid accumulation were measured. Medium was removed, leaving 50 µl in each well. 10 µl Cell Titer Blue reagent was added to each well. Cells were incubated at 37° C. for 2 hours. A 50 µl sample of conditioned medium was removed to a fresh solid black plate. Fluorescence was measured at excitation 560 nm/emission 590 nm. Cells were then washed with PBS and lysed with the lysis buffer. Reagent B was added to each well and the cells were incubated at 37° C. for 2 hours. Aliquots of the lysates were diluted with PBS, then Reagent A was added to each well. The optical density was read at 540 nm after 15 minutes. The reagent measures the amount of glycerol liberated from triglyceride.

Example 29

Effect of *Annona* Extract on Human Preadipocyte Differentiation

The lipid accumulation assay of Example 28 was carried out with *Annona squamosa* extracts. Briefly, six concentrations of *Annona* extracts (0.1, 0.5, 1, 5, 10 and 15 µg/ml) and DMSO 0.10%, TNF-α (0.01 µg/mL) and PPAR-γ agonist (10 µM) as controls were used to treat human subcutaneous adipocytes during the differentiation period. After 2 weeks of treatment, cells were washed with PBS, lysed and triglyceride measured by total TG assay kit (Zen-bio). The reagents contain microbial lipase and the amount of glycerol liberated from triglyceride was measured.

TABLE 31

Effect of *Annona squamosa* Extracts on Preadipocyte Differentiation

| | Treatment Dose/Concentration of Glycerol (µM) | | | | | | | | |
| --- | --- | --- | --- | --- | --- | --- | --- | --- | --- |
| | Control | 10 µM | 0.01 µg/ml | 0.1 µg/ml | 0.5 µg/ml | 1 µg/ml | 5 µg/ml | 10 µg/ml | 15 µg/ml |
| Control | 208.28 | | | | | | | | |
| PPAR-γ | | 226.71 | | | | | | | |
| TNF-α | | | 4.40 | | | | | | |
| Anona | | | | 73.51 | 29.74 | 33.77 | 24.56 | 22.83 | 25.71 |

As shown in Table 31, *Annona* extracts exhibited 64.71%-89.04% inhibition of differentiation of preadipocyte into adipocyte in a dose dependent manner at concentrations ranging from about 0.1 µg/ml to about 15 µg/ml.

Example 30

Effect of *Annona*:Rosemary:*Zanthoxylum* Combination (ARZ-21) on Human Preadipocyte Differentiation The lipid accumulation assay of Example 28 was carried out with combination (ARZ-21) of *Annona*, Rosemary and *Zanthoxylum*. Briefly, six concentrations of the combination (1, 5, 10, 15, 20 and 25 µg/ml) and DMSO (0.10%), TNF-α (0.01 µg/mL) and PPAR-γ agonist (10 µM) as controls were used to treat human subcutaneous adipocytes during the differentiation period. After 2 weeks of treatment cells were washed with PBS, lysed and triglyceride measured by total TG assay kit (Zen-bio). The reagents contain microbial lipase and the amount of glycerol liberated from triglyceride was measured.

TABLE 32

Effect of ARZ-21 Product on Human Preadipocyte Differentiation

| | Treatment Dose/Concentration of Glycerol | | | | | | | | |
| --- | --- | --- | --- | --- | --- | --- | --- | --- | --- |
| | Control | PPAR-γ | TNF-α | 1 µg/ml | 5 µg/ml | 10 µg/ml | 15 µg/ml | 20 µg/ml | 25 µg/ml |
| Control | 208.28 | | | | | | | | |
| PPAR-γ | | 226.71 | | | | | | | |
| TNF-α | | | 4.40 | | | | | | |
| ARZ-21 | | | | 152.99 | 45.29 | 33.77 | 28.59 | 24.56 | 18.80 |

As shown in Table 32, the ARZ-21 combination inhibits the differentiation of human preadipocyte into adipocyte in a dose dependent manner at concentrations ranging from about 1 µg/ml to about 25 µg/ml with 26.55% to 90.97% inhibition.

Example 31

Effect of *Annona*:Rosemary Extract Combinations on Intracellular Triglyceride Content For triglyceride (TG) content assay, 3T3-L1 pre-adipocytes were treated with combinations at concentrations of 2.5, 5 and 10 µg/ml in 6 well plates during adipocyte differentiation for 8 days. The cells were washed with PBS, scraped with homogenizing solutions. The residual cell lysate was centrifuged at 3000 g for 5 min to remove fat layers. The supernatants were assayed. The triglyceride levels were measured by using a commercial kit according to the manufacturer's instructions (#10010303, Cayman Chem., USA). As adipocytes differentiate, their intracellular levels of triglyceride increase continuously.

TABLE 33

Effect of *Annona*:Rosemary Combination on Intracellular Triglyceride Level

| Samples | | Inhibition (%) | | | |
|---|---|---|---|---|---|
| | | 10 ng/ml | 2.5 µg/ml | 5 µg/ml | 10 µg/ml |
| TNF-α | | 55.1 | — | — | — |
| RO-EEd12 (60%) | AS-SCd2 (2% SA1) | — | 50.5 | 76.1 | 79.2 |
| | AS-SCd2 (1% SA1) | — | 0.0 | 58.8 | 71.7 |
| | AS-SCd2 (0.5% SA1) | — | 0.0 | 34.8 | 66.4 |
| RO-EE12 (30%) | AS-SCd2 (2% SA1) | — | 44.9 | 72.5 | 67.3 |
| | AS-SCd2 (1% SA1) | — | 0 | 68.9 | 67.4 |
| | AS-SCd2 (0.5% SA1) | — | 0 | 0 | 71.9 |

As shown in Table 33, all combinations effectively prevented triglyceride accumulation in differentiating 3T3-L1 pre-adipocytes and showed more than 60% of inhibition effect at a dose of 10 µg/ml. The data show that the efficacy increased in relation to the amount of *Annona squamosa* in the combination compositions.

Example 32

Ant-Oxidant Effect of Carnosic Acid-Enriched Rosemary Extracts

The stable free radical 1,1-diphenyl-2-picryl-hydrazyl (DPPH) was used to examine the free radical scavenging activity of Rosemary extract samples. Briefly, a 0.2 mM solution of DPPH was prepared in DMSO, which was mixed with each extract sample at concentrations of 1, 5, 10, 20 and 40 µg/ml. After a 30 min. incubation in the dark, absorbance was measured at 517 nm with a spectrophotometer. A decrease in solution absorbance indicates a decrease of DPPH and an anti-oxidant effect. The anti-oxidant activity is expressed as a percent inhibition.

TABLE 34

Anti-Oxidant Activity of Carnosic Acid-Enriched Rosemary Extracts

| | Inhibition (%) | | | | |
|---|---|---|---|---|---|
| Samples | 1 µg/ml | 5 µg/ml | 10 µg/ml | 20 µg/ml | 40 µg/ml |
| RO-EE12 (60%) | 0.5 ± 1.9 | 13.6 ± 0.6 | 38.4 ± 0.6 | 85.2 ± 0.6 | 91.8 ± 0.2 |
| RO-EE12 (30%) | 0.0 ± 1.1 | 0.0 ± 1.1 | 15.5 ± 0.6 | 41.4 ± 1.0 | 81.9 ± 0.1 |
| RO-EEd12 (60%) | 0.6 ± 1.3 | 11.2 ± 2.8 | 44.0 ± 0.1 | 88.8 ± 1.0 | 92.1 ± 0.1 |
| RO-EEd12 (30%) | 0.0 ± 0.9 | 1.0 ± 1.2 | 16.5 ± 0.1 | 48.1 ± 0.4 | 88.1 ± 0.2 |

As shown in Table 34, all Rosemary extracts showed an anti-oxidant effect in a dose dependent manner and 60% carnosic acid showed a greater anti-oxidant effect than 30% carnosic acid. The efficacy was maintained even after the decolorization process.

Example 33

Vasorelaxation Assay Using Rat Aorta Rings

Thoracic aortas isolated from male Sprague Dawley rats were placed into Krebs buffered solution aerated with 95% $O_2$/5% $CO_2$ (37° C., pH 7.4). The attached fat and adherent periadventitial tissue were cleaned carefully and the vessels were cut into four rings 2-3 mm long. Aorta rings were mounted on two triangular stainless steel wire specimen holders and transferred to 7.5 mL organ bath filled with Krebs buffered solution aerated with 95% $O_2$/5% $CO_2$ (37° C., pH 7.4). Each ring was attached to a fixed glass hook in the tissue bath and through a weightless wire hook to a force transducer connected to the four channel myograph (DMT DK/610M, Denmark) for the measurement of isometric force. Changes in isometric force were recorded on a personal computer through the use of a system integrator software program (Analog-to digital converter, Powerlab 8/30, Adinstruments Co.) and Data acquisition software (Chart 6.0, Adinstruments Co). Rings were placed on passive tension to yield a preload of 2.0 g and allowed to equilibrate at this tension for 1 hour. During this period, tissues were washed with fresh aerated buffer twice, and the resting force on the rings was adjusted until the set preload of 2.0 g was maintained. Each ring was contracted with cumulative applications of 300 nM phenylephrine. The presence of viable endothelium was assessed in all preparations by determining the ability of acetylcholine (ACh, 1 nM to about 10 µM) to induce more than 80% of relaxation of rings in the presence of phenylephrine.

Example 34

Effect of *Zanthoxylum* Extract on Rat Aortic Ring Contraction

Aortic rings were treated with four different doses of *Zanthoxylum* extract (produced as described in Example 18), as follows: 30 µg/ml, 100 µg/ml, 300 µg/ml, and 1,000 µg/ml. After treatment with each dose of the *Zanthoxylum* extract, the aortic rings were washed three times over a 30 minute period with Krebs buffer (37° C., pH 7.4) to bring the aortic tension down to or slightly below the original pre-load level. The vascular relaxant effects of *Zanthoxylum* extract were measured as the percent inhibition of contraction induced by pretreatment with phenylephrine (300 nM) in the isolated rat aortic preparations.

TABLE 35

Vasorelaxant Activity of *Zanthoxylum* Extract

| | *Zanthoxylum* Dose | | | | |
|---|---|---|---|---|---|
| | 0 | 30 µg/ml | 100 µg/ml | 300 µg/ml | 1000 µg/ml |
| % Contraction | 100 | 100 | 100 | 60 | 25 |

Table 35 shows that the *Zanthoxylum* extract exhibited up to 75% vasorelaxant activity in the phenylephrine-induced contraction of rat aorta in a dose dependent manner.

Example 35

Effect of *Annona* Extract on Rat Aortic Ring Contraction

Aortic rings were treated with four different amounts of *Annona squamosa* (sugar apple) extract supernatant AS-EA8S compositions, as follows: 0.0030%, 0.01%, 0.03%, and 0.1% (all v/v). After treatment each dose of *Annona* extract, the aortic rings were washed three times over a 30 minute period with Krebs buffer (37° C., pH 7.4) to bring the aortic tension down to or slightly below the original pre-load level. The vascular relaxant effects of *Annona* extract treatment was measured as the percent inhibition of contraction induced by pre-treatment with phenylephrine (300 nM) of isolated rat aortic preparations.

TABLE 36

Effect of *Annona* Extract Supernantant on Vasorelxation

| AS-EA8S Dose | 0 | 0.003%, v/v | 0.01%, v/v | 0.03%, v/v | 0.1%, v/v |
|---|---|---|---|---|---|
| % Contraction | 100 | 95% | 75% | 45% | 20% |

The *Annona* extract supernatant exhibited greater than 80% vasorelaxant activity in a concentration dependent manner in a phenylephrine-induced contraction of rat aorta.

Example 36

Anti-Platelet Aggregation Assay

Whole blood from male Sprague Dawley rats was collected into 15 mL test tubes containing 1 mL of anticoagulant citrate/dextrose solution (ACD, 85 mM trisodium citrate, 83 mM dextrose, and 21 mM citric acid). Blood was centrifuged at 170×g for 7 min. to obtain platelet-rich plasma, which was further centrifuged at 120×g for 7 min to remove residual erythrocytes. This platelet-rich plasma was centrifuged twice more at 350×g with a washing buffer for 10 min. to remove the ACD solution, and then platelet precipitates were adjusted to (3×108/mL) for aggregation assay in Tyrode buffer (137 mM of NaCl, 12 mM of NaHCO3, 5.5 mM of glucose, 2 mM of KCl, 1 mM of MgCl2, 0.3 mM of NaHPO4, and pH 7.4). Aggregation was monitored by measuring light transmission in an aggregometer (Chronolog, Havertown, Pa., USA). The washed platelets were preincubated at 37° C. for 2 min. with either a test sample or vehicle (<0.1%), and then stimulated with agonists. The reaction mixture was further incubated for 5 min., with stirring at 170×g.

Example 37

Effect of *Zanthoxylum* Extract on Platelet Aggregation

The washed platelets prepared as described in Example 33 were pre-incubated at 37° C. for 2 min with either *Zanthoxylum* extract ZA-EEd18 or vehicle (<0.1%), and then stimulated with adenosine diphosphate (ADP). ADP is a well-known soluble agonist of platelet aggregation and thrombus formation. The reaction mixture was incubated for an additional 5 minutes, with stirring at 170×g.

TABLE 37

Effect of *Zanthoxylum* on Platelet Aggreagation

| *Zanthoxylum* ZA-EEd18 | 500 µg/ml |
|---|---|
| % Aggregation Inhibition | 20% |

The *Zanthoxylum* extract showed an ability to inhibit ADP-induced platelet aggregation.

Example 38

Effect of *Annona* Extract on Platelet Aggregation

The washed platelets prepared as described in Example 36 were pre-incubated at 37° C. for 2 min with either *Annona* extract supernatant AS-EARS or vehicle (<0.1%), stimulated with ADP, and then incubated for an additional 5 min with stirring at 170×g.

TABLE 38

Effect of *Annona* Extract on Platelet Aggregation

| *Annona* AS-EA8S | 250 µg/ml |
|---|---|
| % Aggregation Inhibition | 25% |

The *Annona* extract showed an ability to inhibit ADP-induced platelet aggregation.

Example 39

Effect of Rosemary Extract on Platelet Aggregation

The washed platelets were preincubated at 37° C. for 2 min with either carnosic acid-enriched Rosemary extract (30% or 60%) (prepared as described in Example 14) or vehicle (<0.1%), stimulated with ADP, and then incubated for an additional 5 min. with stirring at 170×g.

TABLE 39

Effect of Rosemary Extracts on Platelet Aggreagation

| Dose | 0 | 12.5 µg/ml | 25 µg/ml | 50 µg/ml | 100 µg/ml |
|---|---|---|---|---|---|
| Rosemary (30% CA) | 100% | 100% | 100% | 80% | 20% |
| Dose | 0 | 7.8 µg/ml | 15.6 µg/ml | 31 µg/ml | 62.5 µg/ml |
| Rosemary (60% CA) | 100% | 95% | 42% | 20% | 32% |

Both 30% carnosic acid and 60% carnosic acid showed a dose dependent inhibition of ADP-induced platelet aggregation in rat platelets.

Example 40

Nitric Oxide Assay

RAW264.7 (Korean Cell Line Bank, South Korea) were cultured and maintained in Dulbecco's modified Eagle's medium (DMEM) (Dalseogu, South Korea) enriched with 10% heat-inactivated fetal bovine serum (WelGene Co., South Korea), 100 µg/ml streptomycin, and 100 U/ml penicillin (Lonza, Md., USA) in a humidified atmosphere of 5% $CO_2$ at 37° C. Cultured RAW264.7 cells ($4 \times 10^5$) were pre-treated with or without the test sample (1, 3, 10 µg/ml) for 30 min. and then stimulated with lipopolysaccharide (LPS, 0.1 µg/ml) for 18 h in a 96 well plate. The cell culture supernatant (100 µl) was mixed with an equal volume of Griss reagent (1% sulphanilamide in 5% phosphoric acid ($H_3PO_4$) and 0.1% N-1-naphthylenediamine dihydrochloride (NEDHC) in deionized distilled water, and then the plates were read at 540 nm in an ELISA reader. The accumulated nitrite in the culture medium was quantified using a standard of $NaNO_2$ (1 mM)

Example 41

Effect of *Annona* Extract on Nitric Oxide Production

Overproduction of NO in macrophages is a hallmark of inflammation. Therefore, the effect of *Annona* extract (25 µg/ml, 50 µg/ml, and 100 µg/ml, prepared according to Example 10) on inhibiting nitric oxide production RAW264.7 cells stimulated to produce NO by treatment with LPS (0.1 µg/ml).

TABLE 40

Effect of *Annona* Extract on LPS-Stimulated Cells

|  | LPS | Annona | | | |
|---|---|---|---|---|---|
|  | Control | Induced | 25 µg/ml | 50 µg/ml | 100 µg/ml |
| NO production (µM) | 1 µM | 28 µM | 15 µM | 12 µM | 7 µM |

*Annona* (sugar apple) extract potently inhibited NO release in a dose dependent manner and without any detectable cytotoxic effect.

Example 42

Effect of Rosemary Extract on Nitric Oxide Production

Overproduction of NO in macrophages is a hallmark of inflammation. Therefore, the effect of carnosic acid-enriched (30% and 60%) Rosemary extract (6.25 µg/ml, 12.50 µg/ml, and 25 µg/ml, prepared according to Example 14) on inhibiting nitric oxide production RAW264.7 cells stimulated to produce NO by treatment with LPS (0.1 µg/ml).

TABLE 41

Effect of Rosemary Extract on NO Production

| Sample | NO production (µM) |
|---|---|
| Control | 1 |
| LPS induced | 28 |
| 30% CA (6.25) | 18 |
| 30% CA (12.5) | 10 |
| 30% CA (25) | 2 |
| 60% CA (6.25) | 8 |
| 60% CA (12.5) | 1 |
| 60% CA (25) | 1 |

Carnosic acid-enriched Rosemary extract potently inhibited NO release in a dose dependent manner and in the absence of any detectable cytotoxic effect.

Example 43

Cream and Lotion Formulations of *Annona*, Rosemary and *Zanthoxylum* Extracts

The active plant extracts from *Annona* (prepared according to Example 10), *Zanthoxylum* (prepared according to Example 18), Rosemary (prepared according to Example 14), or any combination thereof were formulated in liquid, cream and lotion formulas as provided in the following tables.

TABLE 42

Ingredient List in Cream/Lotion Formulations

| Extract | Extract Source | Active Content | $IC_{50}$ (µg/ml) | % (ppm) Cream | Amount in 6 oz (200 g) Cream/Lotion |
|---|---|---|---|---|---|
| Annona | Fruit | 1% Acetogenin | 0.375 | 0.05-0.5% (500-5K ppm) | 100 mg |
| Rosmarinus | Leaf | 60% Carnosic Acid | 10 | 0.1%-2% (1000-20K ppm) | 200 mg |
| Zanthoxylum | Bark | 3% Alkaloids | 300 | 1%-6% (10,000-60K ppm) | 2,000 mg |

TABLE 43

Liquid Formula of *Annona* Extract

| Ingredient | % by Weight |
|---|---|
| Deionized water (Purified) | 88.3 |
| Polysorbate 80 | 5 |
| X0-Therm | 5 |
| Phenoxyethanol | 1 |
| *Annona* extract | 0.5 |
| Potassium Sorbate | 0.2 |

TABLE 44

Liquid Formula of 60% Carnosic Acid-Enriched Rosemary Extract

| Ingredient | % by Weight |
|---|---|
| X0-Therm (PEG-4 and PEG 8 and PVP) | 70 |
| Deionized water (Purified) | 15 |
| Transcutol (Ethoxydiglycol) | 10 |
| Phenoxyethanol | 1 |

TABLE 44-continued

Liquid Formula of 60% Carnosic Acid-Enriched Rosemary Extract

| Ingredient | % by Weight |
|---|---|
| Rosemary extract | 2 |
| Ethanol, undenatured 200 proof | 2 |

TABLE 45

Liquid Formula of *Zanthoxylum* extract

| Ingredient | % by Weight |
|---|---|
| Deionized (Purified) water | 87.55 |
| *Zanthoxylum* extract | 6 |
| Propylene Glycol | 5 |
| Phenoxyethanol | 1.2 |
| Potasiuum sorbate | 0.25 |

TABLE 46

Cream Formula of *Annona* Extract

| Ingredient | % by Weight |
|---|---|
| Deionized (Purified) water | 72.7 |
| Keltrol CG-SFT | 0.3 |
| Botanistat PF-64 | 1 |
| PEG-200 | 5 |
| Polysorbate-40 | 1.5 |
| Polawax | 9 |
| Montanov-68 | 1.5 |
| Caprylic/Capric triglyceride | 6 |
| Cetearyl Alcohol | 0.5 |
| Dimethesil-100 | 1 |
| Sepigel 305 | 1 |
| *Annona* extract | 0.5 |

TABLE 47

ARZ-21 Lotion Formula I

| Ingredient | % by Weight |
|---|---|
| Deionized water (Purified) | 86.35 |
| Botanistat PF-64 | 1 |
| d-*Zanthoxylum* extract | 1 |
| d-*Annona* extract | 0.05 |
| Finsolv TN-0 | 8 |
| Dimethicone-100 | 0.5 |
| Rosemary extract | 0.1 |
| Sepigel 305 | 3 |

TABLE 48

ARZ-21 Lotion Formula II

| Ingredient | % by Weight |
|---|---|
| Deionized water (Purified) | 83.8 |
| Botanistat PF-64 | 1 |
| d-*Zanthoxylum* extract | 1 |
| d-*Annona* extract | 0.05 |
| Ethylhexyl stearate | 10 |
| Cetearyl Alcohol | 0.5 |
| Dimethicone-100 | 0.5 |
| Rosemary extract | 0.1 |
| Sepigel 305 | 3 |
| Rosemary Moroccan | 0.016 |
| Geranimum Rose Egyptian | 0.018 |
| Lavender Bulgarian | 0.016 |

Example 44

A Randomized, Controlled Human Clinical Study Evaluating the Effect of an Anti-Cellulite Topical Cream In an eight week clinical trial comprising a randomized, controlled study, the effect of an anti-cellulite topical cream (comprising extracts from *Annona*, Rosemary, and *Zanthoxylum*) will be evaluated. After four and eight weeks of use, the following will be evaluated, whether there is: (a) a reduction in the appearance of cellulite, (b) improvement in the appearance of waist, arm, hip, and thigh skin contours and tone, (c) aid in the appearance of a slimmer waist, hips, and thighs, (d) improvement in body mass index (BMI), (e) improvement in body fat content in the waist, hips and thighs (caliper method), (0 improvement in skins elasticity and firmness, and (g) an increase in skin moisture (moisture meter). Appearance cellulite and improvement of associated parameters will be measured by visual grading, instrument measurments, and questionnaires. The trial will be performed on generally healthy females (n=40), any race or skin type, composed of two groups of 20 (one group receiving the test product and the other group receiving placebo). Baseline cellulite will be measured on day 0 (must have a visual analog scale (VAS)≥2), week 1, week 2, week 4, and week 8.

TABLE 49

Data Analysis for Clinical Study

| DATA ANALYSIS | Product Evaluation (compared to Placebo) Instrumental and Visual evaluations: Mean and standard deviation of instrumental and visual scores from all time points will be examined and compared between groups utilizing an un-paired t-test. Significance will be set at $p < 0.05$. The percent improvement of mean values for each time point compared to baseline means will be identified. The percentage of subjects improving will be identified. Self-assessment questionnaires Percentage of respondent answers for each time point will be examined (i.e., frequency tables for each group) and compared between groups utilizing Wilcoxon rank sum test. Product Evaluation (compared to baseline, i.e., monadic evaluation) Instrumental and Visual evaluations Mean and standard deviation of instrumental, visual scores from all time points will be examined and compared to baseline utilizing paired t-test. Significance will be set at $p < 0.05$. The percent improvement of mean values for each time point compared to baseline means will be identified. The percentage of subjects improving will be identified. |
|---|---|

Results

In an eight-week, single-blind, randomized, controlled study the ARZ-21 lotion composition described in Example 21 was evaluated in a cohort 40 subjects. Test product or active comparator was assigned to each subject per a randomization code. The product was used by each subject according to instructions provided for a period of eight weeks. Skin condition of subjects' thighs was evaluated by expert clinical grading using a standard ordinal scale and visual analogue scales (VAS). Instrumental assessments including caliper measurements, INBODY, Cutometer, Corneometer and silicone replica casting and analysis were performed. Photographs of skin on all subjects' thighs were also taken. Consumer perception of product efficacy was collected utilizing subject questionnaires. Visits occurred at Baseline and after two, four and eight weeks of product use.

The purpose of the study was to evaluate product efficacy after two, four and eight weeks of use, as assessed by expert visual grading and subjective questionnaires. Data was collected and analyzed with specific regard to the following proposed product features:

1. Reduced appearance of cellulite;
2. Improved appearance of upper thigh area skin contours and tone (firmness);
3. Aided in the appearance of a slimmer upper thigh area;
4. Improved body mass index (BMI) (assessed by INBODY BMI measurement);
5. Improves body fat content in the upper thigh area (assessed by body fat assessments; caliper method in each region);
6. Improved skin elasticity and firmness (assessed by visual grading, Cutometer); and
7. Increased skin moisture content (assessed by Corneometer)

Inclusion Criteria

1. Females of any race and skin type, in good general health, eighteen to fifty-nine years old, inclusive at time of enrollment.
2. Able to read, understand and sign an informed consent, understand and willing to follow study instructions and complete a brief personal/medical history.
3. Mild to severe cellulite on thighs, scoring greater than or equal to 2 on a standard ordinal scale at the Baseline assessment.
4. Willing to abstain from extended periods of sun exposure of the skin of both thighs and all use of artificial tanning for the duration of the study.
5. Willing to refrain from beginning the use of any skin treatment products on thighs, including moisturizers, creams and cleansers, other than the assigned test materials, for the duration of the study.
6. Willing to arrive at the clinic wearing black underwear (same at each study visit) and willing to change into loose fitting shorts (provided by the subject) and willing to remove shorts for assessments and photography.

Exclusion Criteria

1. Pregnant, breast-feeding, or planning a pregnancy during the study period.
2. Participating in any other clinical studies.
3. Any history of sensitivity to skin treatment products or known allergies to personal care products (self-reported).
4. Any condition(s) apparent at entry or recognized after entry that are likely to invalidate a subject's consent to participate in this study and/or limit the ability of a subject to regularly attend all study visits or to comply with all other protocol requirements such as: diseases, injuries, alcoholism, drug abuse, psychosis, antagonistic personality, poor motivation, infirmity disability, other problems that may be emotional, intellectual, psychological or social.

5. Any other condition(s) considered by the investigator as sound reason for disqualification from enrollment into the study.

The eight-week clinical study included four visits: one for Baseline screening, qualification and evaluations, and three for Week 2, Week 4 and Week 8 evaluations.

TABLE 50

Procedure Summary

| Procedure | | Baseline | Week 2 | Week 4 | Week 8 |
|---|---|---|---|---|---|
| Consent and medical history | | X | | | |
| Inclusion/Exclusion criteria reviewed | | X | | | |
| Dispense (D)/Collect (C) Products | | D | | | C |
| Expert Grader Assessments for Efficacy | Texture/Smoothness Firmness Elasticity Cellulite | X | X | X | |
| INBODY | | X | X | X | X |
| Silicone Replica Casting | | X | | X | X |
| Body Fat Calipers | | X | X | X | X |
| Cutometer | | X | X | X | X |
| Photography | | X | X | X | X |
| Corneometer | | X | X | X | X |
| Subject Questionnaire | | | X | X | X |
| Diary, product and instructions administered | | X | | | |
| Diary and Compliance reviewed | | | X | X | X |
| Adverse Experience reporting | | | X | X | X |
| Subject payment | | | | | X |
| Materials returned and subject dismissed | | | | | X |

Product Evaluation (Test Product Versus Active Comparator)

Instrumental and Visual Evaluations:

Mean and standard deviation of instrumental and visual scores from all visits were provided and compared between groups utilizing an un-paired t-Test. Significance was set at $p<0.05$.

The mean percent difference of instrumental and visual scores from Baseline for each visit, will provided and compared between groups utilizing an un-paired t-Test. Significance will be set at $p<0.005$.

The mean percent improvement of individual scores from Baseline results will be presented for each visit.

The percent of subjects' scores improving from Baseline results will be presented for each visit.

Self-Assessment Questionnaires:

Response frequency percent were tabulated for each question at each visit and product group data compared utilizing the Wilcoxon Rank Sum Test or a Chi-Square test depending on structure of questionnaire.

TABLE 51

Expert Clinical Grader Evaluation - Monadic, comparison to Baseline.

| | | ARZ-21 Lotion | | | | Active Comparator lotion | | | |
|---|---|---|---|---|---|---|---|---|---|
| Assessment | Time Point | n | Mean ± SD | % of Subjects Showing Improvement From BL | P-Value TX vs. BL | n | Mean ± SD | % of Subjects Showing Improvement From BL | P-Value TX vs. BL |
| Texture/ Smoothness | Baseline | 19 | 4.41 ± 2.12 | | | 21 | 4.88 ± 1.71 | | |
| | Week 2 | 18 | 4.42 ± 2.37 | 55.6% | 0.747 | 21 | 4.91 ± 2.19 | 42.9% | 0.925 |
| | Week 4 | 18 | 4.91 ± 2.44 | 27.8% | 0.064 | 18 | 4.99 ± 2.42 | 55.6% | 0.984 |
| | Week 8 | 19 | 5.09 ± 2.23 | 36.8% | 0.076 | 21 | 4.76 ± 2.27 | 52.4% | 0.792 |
| Firmness | Baseline | 19 | 4.79 ± 2.83 | | | 21 | 5.51 ± 2.01 | | |
| | Week 2 | 18 | 4.76 ± 2.62 | 66.7% | 0.583 | 21 | 5.18 ± 2.35 | 57.1% | 0.500 |
| | Week 4 | 18 | 5.01 ± 2.51 | 38.9% | 0.255 | 18 | 5.05 ± 2.53 | 61.1% | 0.198 |
| | Week 8 | 19 | 5.13 ± 2.51 | 47.4% | 0.328 | 21 | 4.58 ± 2.30 | 66.7% | 0.054 |
| Elasticity (tactile) | Baseline | 19 | 4.77 ± 2.36 | | | 21 | 5.56 ± 2.04 | | |
| | Week 2 | 18 | 4.83 ± 2.60 | 61.1% | 0.790 | 21 | 5.21 ± 2.41 | 57.1% | 0.488 |
| | Week 4 | 18 | 5.02 ± 2.53 | 38.9% | 0.249 | 18 | 5.14 ± 2.57 | 61.1% | 0.197 |
| | Week 8 | 19 | 5.06 ± 2.53 | 42.1% | 0.400 | 21 | 4.62 ± 2.31 | 66.7% | 0.059 |
| Cellulite | Baseline | 19 | 2.28 ± 0.60 | | | 21 | 2.28 ± 4.63 | | |
| | Week 2 | 18 | 2.27 ± 0.57 | 11.1% | 0.790 | 21 | 2.14 ± 0.35 | 19.0% | 0.186 |
| | Week 4 | 18 | 2.22 ± 0.64 | 16.7% | 0.483 | 18 | 2.22 ± 0.42 | 16.7% | 0.331 |
| | Week 8 | 19 | 2.23 ± 1.08 | 26.3% | 0.786 | 21 | 2.00 ± 0.82 | 47.6% | 0.104 |

TABLE 52

Instrumental Evaluation - Monadic, comparison to Baseline.

| | | | ARZ-21 Lotion | | | | Active Comparator lotion | | | |
|---|---|---|---|---|---|---|---|---|---|---|
| | Assessment | Time Point | n | Mean ± SD | Percent of Subjects Showing Improvement From BL | P-Value TX vs. BL | n | Mean ± SD | Percent of Subjects Showing Improvement From BL | P-Value TX vs. BL |
| | Corneometer | Baseline | 19 | 17.09 ± 7.91 | | | 20 | 16.55 ± 5.82 | | |
| | | Week 2 | 18 | 20.27 ± 6.27 | 72.2% | 0.024* | 20 | 25.47 ± 7.66 | 95.0% | <0.001* |
| | | Week 4 | 18 | 22.12 ± 7.38 | 77.8% | 0.011* | 17 | 27.77 ± 9.13 | 94.1% | <0.001* |
| | | Week 8 | 19 | 18.70 ± 8.90 | 63.2% | 0.444 | 20 | 22.04 ± 7.84 | 75.0% | 0.001* |
| Cutometer | Firmness (R0, Uf) | Baseline | 18 | 0.15 ± 0.02 | | | 20^ | 0.15 ± 0.23 | | |
| | | Week 2 | 17 | 0.13 ± 0.02 | 88.2% | <0.001* | 20 | 0.13 ± 0.01 | 85.0% | 0.001* |
| | | Week 4 | 18 | 0.11 ± 0.02 | 100% | <0.001* | 17 | 0.11 ± 0.02 | 100% | <0.001* |
| | | Week 8 | 18 | 0.09 ± 0.02 | 100% | <0.001* | 20 | 0.08 ± 0.02 | 100% | <0.001* |
| | Elasticity (R5, Ur/Ue) | Baseline | 18 | 0.27 ± 0.10 | | | 21 | 0.33 ± 0.10 | | |
| | | Week 2 | 17 | 0.24 ± 0.07 | 47.1% | 0.153 | 21 | 0.28 ± 0.11 | 28.6% | 0.031** |
| | | Week 4 | 18 | 0.24 ± 0.06 | 44.4% | 0.088 | 18 | 0.29 ± 0.09 | 22.2% | 0.366 |
| | | Week 8 | 18 | 0.43 ± 0.09 | 94.4% | <0.001* | 21 | 0.47 ± 0.10 | 95.2% | <0.001* |

*Indicates a statistically significant improvement compared to baseline, p ≤ 0.05
**Indicates a statistically significant worsening compared to baseline, p ≤ 0.05

TABLE 53

Consumer Perception - Subjective Questionnaire Week 8.

| | Unigen Lotion | | | Active Comparator Lotion | | | |
|---|---|---|---|---|---|---|---|
| Question | n | Responding Yes | Percent Improvement* | n | Responding Yes | Percent Improvement* | p value |
| Improved skin hydration/moisture? | 19 | 15 (78.9%) | 45.33% | 21 | 16 (76.2%) | 50.00% | 0.607 |
| Improved texture/smoothness? | 19 | 10 (52.6%) | 49.00% | 21 | 14 (66.7%) | 50.71% | 0.313 |
| Reduced the appearance cellulite? | 19 | 9 (47.4%) | 44.44% | 21 | 11 (52.4%) | 42.72% | 0.049 |

TABLE 53-continued

| | Consumer Perception - Subjective Questionnaire Week 8. | | | | | |
|---|---|---|---|---|---|---|
| | Unigen Lotion | | | Active Comparator Lotion | | |
| Question | n | Responding Yes | Percent Improvement* | n | Responding Yes | Percent Improvement* | p value |
| Improved the appearance of upper thigh skin contours and tone? | 19 | 10 (52.6%) | 40.00% | 21 | 14 (66.7%) | 40.17% | 0.338 |
| Improved firmness/elasticity? | 19 | 11 (57.9%) | 39.09% | 21 | 15 (71.4%) | 43.33% | 0.300 |
| Improved overall appearance of a slimmer upper thigh area? | 19 | 9 (47.4%) | 44.44% | 21 | 11 (52.4%) | 45.45% | 0.036 |

*Only subjects responding YES to the question answered Percent Improvement portion of the question.

Study Outcomes

Instrumental Assessment—Cutometer

Statistically significant improvements from mean Baseline score for skin firmness were observed in both product groups at the Week 2, Week 4 and Week 8 visits. Statistically significant improvements from mean Baseline score for skin elasticity were observed in both groups at the Week 8 visit only. A statistically significant decrease (worsening) from mean Baseline score was noted in skin elasticity for Active Comparator Lotion at the Week 2 visit.

Comparative analysis of results from both groups showed no statistically significant differences between their mean change from Baseline scores for either firmness or elasticity.

Silicone Replicas

Statistically significant improvement from mean Baseline score for average roughness (Ra) was observed in the Active comparator Lotion group at Week 4 only. No other significance changes were observed compared to baseline. Comparative analysis of results from both groups showed no statistically significant difference.

Subjective Questionnaire

The number of positive responses grew as a function of time and product use for both ARZ-21 Lotion and Active Comparator Lotion. At Weeks 2, 4 and 8, the majority of subjects (>50%) in the ARZ-21 Lotion Group agreed that the also indicated that the test product improved skin's hydration/moisture and that it improved skin texture/smoothness. At Weeks 4 and 8, the majority of subjects (>50%) in the ARZ-21 Lotion Group agreed that the test product improved skin's texture/smoothness and improved the appearance of upper thigh skin's contours and tone. In Group B at Weeks 4 and 8, the majority also indicated that the ARZ-21 product reduced the appearance of cellulite, improved the appearance of upper thigh skin's contours and tone and improved skin's firmness/elasticity. At Week 8, the majority of subjects (>50%) in ARZ-21 Lotion Group agreed that the test product improved skin's firmness/elasticity. In Comparator Lotion Group at Week 8, the majority also indicated that the test product improved the overall appearance of a slimmer upper thigh area.

Comparative analysis of results from both groups showed statistically significant differences between their mean response scores for questions regarding improvements in cellulite and overall appearance of slimmer upper thigh at all visits, and in skin firmness/elasticity at the Week 2 and Week 4 visits, and in upper thigh skin contours and tone at the Week 2 visit only.

In conclusion, under the conditions of this study, use of ARZ-21 Lotion led to significant improvements in firmness and elasticity. Subject perception of product effects became increasingly positive as a function of time and product use.

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for treating skin comprising topically administering to the skin of a subject in need thereof a composition comprising an effective amount of an *Annona squamosa* fruit extract, wherein the extract comprises an amount of one or more Annonaceous acetogenins;

wherein the one or more acetogenins have a structure according to formula (I), (II), or (III), as follows:

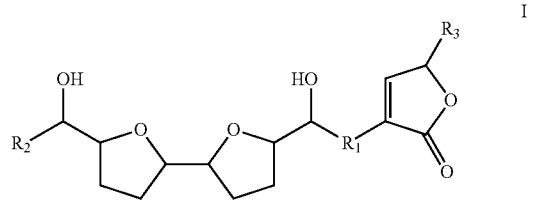

-continued

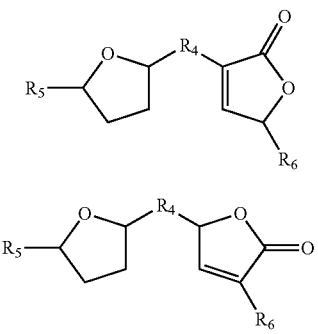

wherein $R_1$-$R_6$ are each independently substituted or unsubstituted $C_{1-50}$ alkyl or $C_{1-50}$ rings and/or having 0-5 tetrahydrofuran rings and/or double and/or triple bonds and/or having along the $C_{1-50}$ alkyl or rings one or more moieties of hydroxyls, acetoxyls, ketones and/or epoxides; and wherein the composition is administered in an amount sufficient to provide an effect selected from the group consisting of: tightening and firming sagging or loose skin; improving tone, elasticity, and/or smoothness of the skin; inhibiting free radical damage; reducing fat synthesis; reducing fat content in cells; reducing fat cell size; reducing or inhibiting cell differentiation into fat cells; promoting fat cell apoptosis; promoting lipolysis; improving fat removal; maintaining or promoting or supporting a healthy lipid profile or cholesterol level; and combinations thereof.

2. The method of claim 1, wherein the *Annona squamosa* fruit extract is decolorized.

3. The method of claim 1, wherein the *Annona squamosa* fruit extract is enriched for squamocin, motrilin, or both.

4. The method of claim 1, wherein the *Annona squamosa* fruit extract comprises from about 0.1% to about 30% acetogenins.

5. The method of claim 1, wherein the composition further comprises an adjuvant, wherein the adjuvant comprises a contouring agent.

6. The method of claim 5, wherein the contouring agent comprises collagen, elastin, or both.

7. The method of claim 1, wherein the composition further comprises a Rosemary extract enriched for terpenes.

8. The method of claim 1, wherein the composition further comprises a *Zanthoxylum* extract enriched for one or more isoquinoline alkaloids.

9. The method of claim 1, wherein the composition is administered topically.

10. The method of claim 1, wherein a biomarker for an *Annona squamosa* fruit extract enriched for one or more acetogenins is kaurenoic acid.

* * * * *